(12) United States Patent
Pitt

(10) Patent No.: US 8,063,038 B2
(45) Date of Patent: Nov. 22, 2011

(54) HETEROCYCLIC CONDENSED COMPOUNDS USEFUL AS ANTIDIURETIC AGENTS

(75) Inventor: Gary Robert William Pitt, Wiltshire (GB)

(73) Assignee: Vantia Limited, Chilworth (GB)

( * ) Notice: Subject to any disclaimer, the term of this patent is extended or adjusted under 35 U.S.C. 154(b) by 859 days.

(21) Appl. No.: 11/660,207

(22) PCT Filed: Aug. 18, 2005

(86) PCT No.: PCT/EP2005/054081
§ 371 (c)(1),
(2), (4) Date: Jun. 16, 2008

(87) PCT Pub. No.: WO2006/018443
PCT Pub. Date: Feb. 23, 2006

(65) Prior Publication Data
US 2008/0234250 A1   Sep. 25, 2008

Related U.S. Application Data

(60) Provisional application No. 60/602,890, filed on Aug. 20, 2004.

(30) Foreign Application Priority Data

Aug. 20, 2004   (EP) ..................................... 04104006

(51) Int. Cl.
*A61K 31/553* (2006.01)
*C07D 498/02* (2006.01)

(52) U.S. Cl. ................. 514/211.1; 514/211.11; 540/548
(58) Field of Classification Search ........................ None
See application file for complete search history.

(56) References Cited

FOREIGN PATENT DOCUMENTS
WO       WO 02/00626 A1     1/2002

OTHER PUBLICATIONS

Kondo. Expert Opinion on Therapeutic Patents, 2002, 12(6), 1249-1258.*

* cited by examiner

*Primary Examiner* — Noble Jarrell
(74) *Attorney, Agent, or Firm* — Woodcock Washburn LLP

(57) ABSTRACT

The invention concerns compounds according to general formulae 1, wherein $G^1$ is an amine. Compounds according to the invention are vasopressin $V_2$ receptor agonists. Pharmaceutical compositions of the compounds are useful as antidiuretic agents.

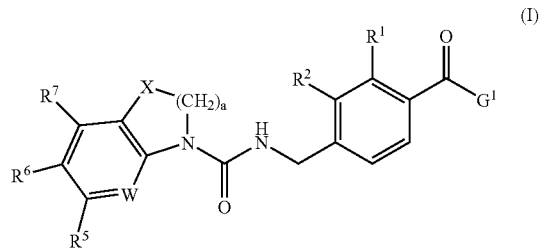

18 Claims, No Drawings

HETEROCYCLIC CONDENSED COMPOUNDS USEFUL AS ANTIDIURETIC AGENTS

CROSS REFERENCE TO RELATED APPLICATIONS

This application is the National Phase of PCT/EP2005/054081, filed Aug. 18, 2005, and published as WO 2006/018443, and claims priority to European Patent Application No. 04104006.4, filed Aug. 20, 2004, and U.S. Provisional Application No. 60/602,890, filed Aug. 20, 2004. The entirety of these applications are incorporated herein by reference.

FIELD OF THE INVENTION

The present invention relates to a class of novel chemical entities which act as agonists of the peptide hormone vasopressin. They reduce urine output from the kidneys and so are useful in the treatment of certain human diseases characterised by polyuria. They are also useful in the control of urinary incontinence and bleeding disorders.

Priority is claimed from EP application number 04104006.4 and U.S. patent application Ser. No. 60/602,890, both having a filing date of 20 Aug. 2004.

BACKGROUND

Vasopressin is a peptide hormone secreted by the posterior pituitary gland. Vasopressin is further described p. 1-3 in the International Patent Application WO 02/00626 with the international publication date 3 Jan. 2002. Vasopressin acts on the kidney to increase water retention and so reduce urine output. For this reason, vasopressin is alternatively known as "antidiuretic hormone". It also acts on the vasculature, where it produces a hypertensive effect. The cellular receptors that mediate these two actions have been characterised and shown to be different. The antidiuretic action is mediated by the type-2 vasopressin receptor, commonly called the $V_2$ receptor. Agents that can interact with the $V_2$ receptor and activate it in the same way as vasopressin are called $V_2$ receptor agonists (or simply $V_2$ agonists). Such agents will have an antidiuretic action. If these agents interact selectively with the $V_2$ receptor and not the other vasopressin receptor subtypes, then they will not have the hypertensive effect of vasopressin. This would be an important safety consideration and make such agents attractive for the treatment of human disease conditions characterised by polyuria (which is herein taken to mean excessive urine production).

There remains a need for alternative $V_2$ agonists. Such compounds may advantageously be easy-to-synthesize non-peptides.

SUMMARY OF THE INVENTION

According to an aspect the present invention concerns the compounds according to formula 1 of claim 1, including tautomers and acceptable salts thereof.

According to another aspect the invention relates to novel $V_2$ agonists.

According to another aspect the invention relates to pharmaceutical compositions comprising at least one compound according to the invention. These compositions may find utility in the treatment of polyuria including polyuria resulting from central diabetes insipidus, nocturnal enuresis, nocturia, control of urinary incontinence, voiding postponement, or treatment of bleeding disorders.

According to another aspect the invention relates to the use of the compounds for the manufacture of a medicament for the treatment of diseases such as polyuria including polyuria resulting from central diabetes insipidus, nocturnal enuresis, nocturia, control of urinary incontinence, voiding postponement and bleeding disorders.

According to further aspects the invention relates to the use of the compounds and compositions of the invention in therapy.

DETAILED DESCRIPTION OF THE INVENTION

The present invention relates to a series of compounds according to general formula 1, and to tautomers and pharmaceutically acceptable salts thereof.

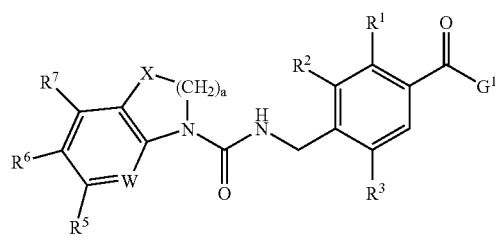

1

In this general formula W is selected from N and $CR^4$;

X is selected from $CH(R^8)$, O, S, $N(R^8)$, $C(=O)$, $C(=O)O$, $C(=O)N(R^8)$, $OC(=O)$, $N(R^8)C(=O)$, $C(R^8)=CH$, and $C(=R^8)$;

$G^1$ is a bicyclic or tricyclic fused azepine derivative selected from general formulae 2 to 9 or an aniline derivative according to general formula 10

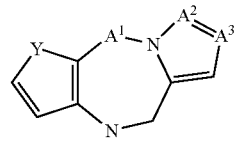

2

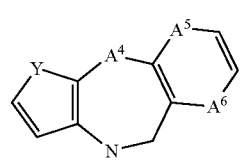

3

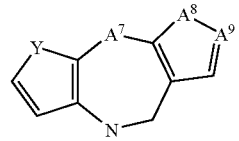

4

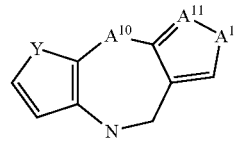

5

-continued

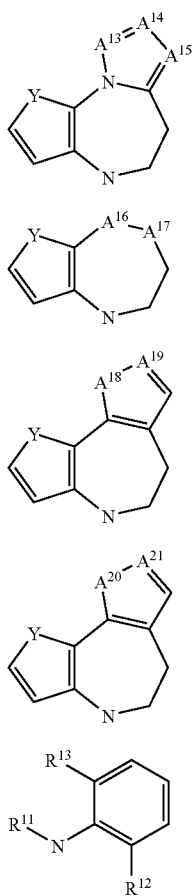

$A^1$, $A^4$, $A^7$ and $A^{10}$ are each independently selected from $CH_2$, C=O, O, and $NT^{10}$;
$A^2$, $A^3$, $A^9$, $A^{11}$, $A^{13}$, $A^{14}$, $A^{15}$, $A^{19}$, and $A^{20}$ are each independently selected from CH and N;
either $A^5$ is a covalent bond, and $A^6$ is S; or $A^5$ is N=CH, and $A^6$ is a covalent bond;
$A^8$, $A^{12}$, $A^{18}$, and $A^{21}$ are each independently selected from CH=CH, NH, $NCH_3$, and S;
$A^{16}$ and $A^{17}$ are both $CH_2$, or one of $A^{16}$ and $A^{17}$ is $CH_2$, and the other is selected from C=O, CH(OH), $CF_2$, O, $SO_c$, and $NR^{10}$;
Y is selected from CH=CH or S;
$R^1$ and $R^2$ are independently selected from H, F, Cl, Br, alkyl, $CF_3$, and O-alkyl;
$R^3$ is selected from H and alkyl;
$R^4$-$R^7$ are independently selected from H, F, Cl, Br, alkyl, $CF_3$, OH, and O-alkyl;
$R^8$ is selected from H, $(CH_2)_b R^9$, and $(C=O)(CH_2)_b R^9$;
$R^9$ is selected from H, alkyl, optionally substituted aryl, optionally substituted heteroaryl, OH, O-alkyl, OC(=O)alkyl, $NH_2$, NHalkyl, $N(alkyl)_2$, CHO, $CO_2H$, $CO_2$alkyl, $CONH_2$, CONHalkyl, $CON(alkyl)_2$, and CN;
$R^{10}$ is selected from H, alkyl, COalkyl, and $(CH_2)_d OH$;
$R^{11}$ is selected from alkyl, $(CH_2)_d Ar$, $(CH_2)_d OH$, $(CH_2)_d NH_2$, $(CH_2)_d COOalkyl$, $(CH_2)_d COOH$, and $(CH_2)_d OAr$;
$R^{12}$ and $R^{13}$ are each independently selected from H, alkyl, F, Cl, Br, $CH(OCH_3)_2$, $CHF_2$, $CF_3$, COalkyl, CONHalkyl, $(CH_2)_d NHCH_2 Ar$, $CON(alkyl)_2$, CHO, COOH, $(CH_2)_d OH$, $(CH_2)_d NH_2$, $N(alkyl)_2$, $CONH(CH_2)_d Ar$, and Ar;

Ar is selected from optionally substituted heterocycles or optionally substituted phenyl;
a is 1, 2 or 3;
b is 1, 2, 3 or 4;
c is 0, 1 or 2; and
d is 0, 1, 2 or 3.

Certain compounds within the scope of the present invention may exist as tautomers. For example, when W is nitrogen and $R^5$ or $R^7$ is a hydroxy group, the resulting hydroxypyridine can exist as the pyridone tautomer. All such tautomers are considered to be within the scope of the present invention.

As used herein, the term "alkyl" is intended to designate lower alkyl groups, i.e. saturated hydrocarbon groups of between one and six carbon atoms, including linear, branched and cyclic alkyl groups. Examples of "alkyl" include, but are not limited to: C1-methyl, C2-ethyl, C3-propyl, isopropyl, cyclopropyl, C4-n-butyl, sec-butyl, isobutyl, tert-butyl, cyclobutyl, cyclopropylmethyl, methylcyclopropyl, C5-n-pentyl, neopentyl, cyclopropylethyl, dimethylcyclopropyl, and C6-n-hexyl, cyclohexyl, bicyclo[3.1.0]hexyl.

The compounds according to the present invention may have one or more stereogenic centres ("asymmetric carbon atoms") and so may exhibit optical isomerism. The scope of the present invention includes all epimers, enantiomers and diastereoisomers of compounds according to general formula I, including single isomers, mixtures and racemates.

Certain compounds of general formula 1 are capable of forming salts with acids or bases. For example, compounds containing one or more basic nitrogen atoms can form addition salts with mineral and organic acids such as hydrochloric acid, sulphuric acid, phosphoric acid, acetic acid, trifluoroacetic acid, methanesulphonic acid, citric acid and benzoic acid. Compounds containing acidic groups can form salts with bases. Examples of such salts include the sodium, potassium, calcium, triethylammonium and tetraethylammonium salts. Furthermore, compounds that have both acidic and basic groups can form internal salts (zwitterions). Insofar as these salts are pharmaceutically acceptable, they are included within the scope of the invention.

According to aspects of the invention, preferred embodiments of the invention are as set out below.

These aspects comprise instances where $G^1$ is selected from

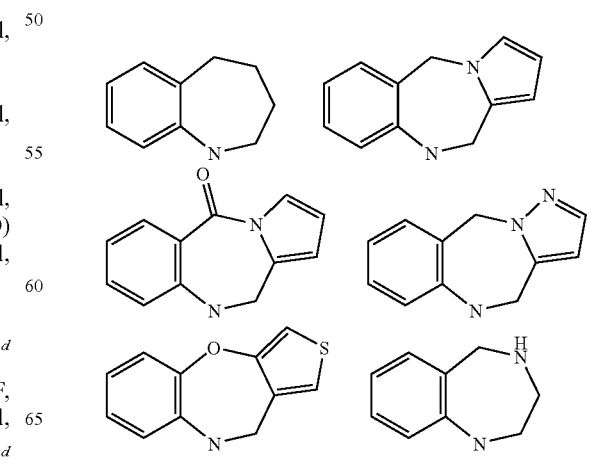

-continued

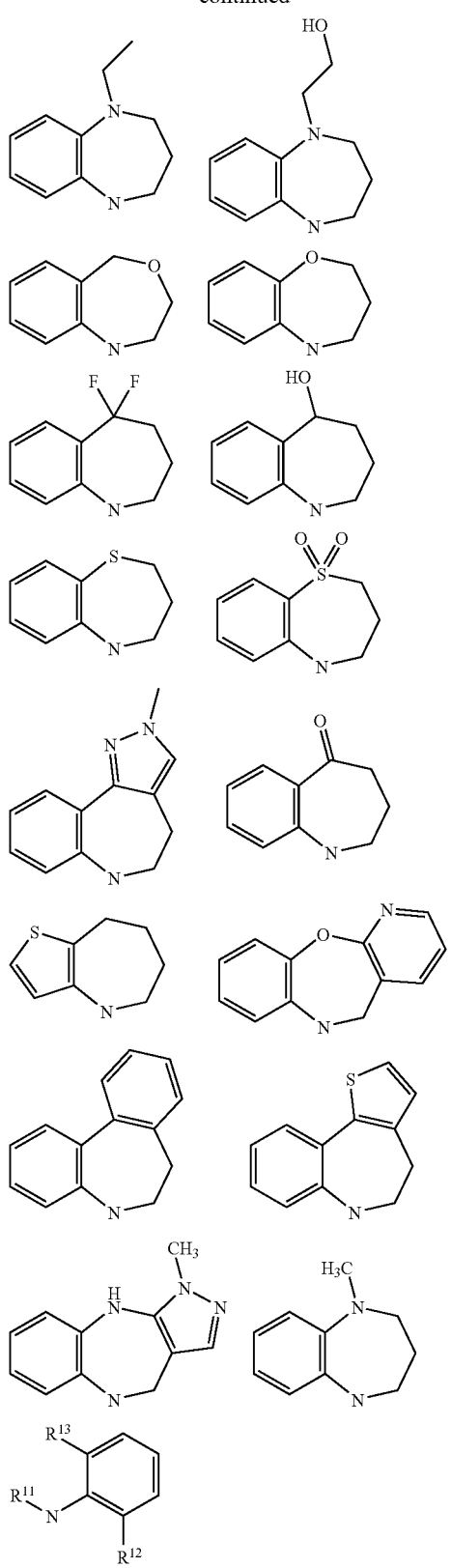

wherein R[11], R[12] and R[13] are as previously defined.

Further preferred is the compound wherein G[1] is selected from:

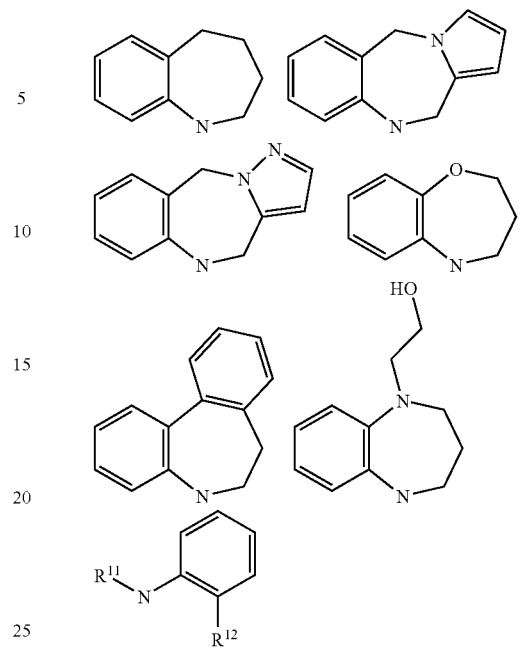

wherein R[11] and R[12] are as previously defined.

More preferred is when G[1] is selected from:

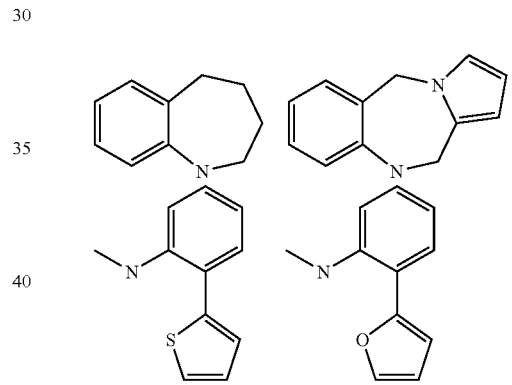

Preferred is the compound, wherein at least one of R[1], R[2], and R[3] is not H.

Further preferred is the compound, wherein one of R[1], R[2], and R[3] is methyl, Cl or F, and the rest are H.

More preferred is the compound, wherein R[2] is methyl or Cl, and R[1] and R[3] are both H.

Preferred is the compound, wherein W is C—F, C—Cl or C—Br.

More preferred is the compound, wherein W is C—F.

Preferred is the compound, wherein X is N(R[8])C(=O), and a is 1.

More preferred is the compound, wherein X is N(R[8])C(=O), R[8] is (CH$_2$)$_b$R[9], and a is 1.

Preferred is the compound, wherein R[5] is either H or F, and both R[6] and R[7] are H.

Preferred is the compound, wherein W is CR[4], X is N(R[8])C(=O), R[1] is H, R[2] is methyl or Cl, R[3] is H, R[4] is F, and R[5], R[6], and R[7] are H, and a is 1.

Preferred is the compound, wherein G[1] is a group according to general formula 7, wherein Y is CH=CH, A[16] is CH$_2$, A[17] is CH$_2$, R[1] is H, R[2] is methyl or Cl, and R[3] is H.

Preferred is the compound, wherein G¹ is a group according to general formula 2, wherein Y is CH=CH, A¹ is CH₂, both A² and A³ are CH, R¹ is H, R² is methyl or Cl, and R³ is H.

Particularly preferred is a compound selected among the group consisting of
{1-[4-(5H,11H-Benzo[e]pyrrolo[1,2-a][1,4]diazepine-10-carbonyl)-2-methylbenzylcarbamoyl]-8-fluoro-1,2,3,4-tetrahydroquinolin-4-yl}acetic acid ethyl ester;
{4-[4-(5H,11H-Benzo[e]pyrrolo[1,2-a][1,4]diazepine-10-carbonyl)-2-methylbenzylcarbamoyl]-5-fluoro-2-oxo-3,4-dihydro-2H-quinoxalin-1-yl}acetic acid methyl ester;
{5,6-Difluoro-4-[2-methyl-4-(2,3,4,5-tetrahydrobenzo[b]azepine-1-carbonyl)benzylcarbamoyl]-2-oxo-3,4-dihydro-2H-quinoxalin-1-yl}acetic acid;
{5-Chloro-4-[2-methyl-4-(2,3,4,5-tetrahydrobenzo[b]azepine-1-carbonyl)benzylcarbamoyl]-2-oxo-3,4-dihydro-2H-quinoxalin-1-yl}acetic acid;
{5-Fluoro-4-[2-methyl-4-(2,3,4,5-tetrahydrobenzo[b]azepine-1-carbonyl)benzylcarbamoyl]-2-oxo-3,4-dihydro-2H-quinoxalin-1-yl}acetic acid;
{6-Fluoro-5-[2-methyl-4-(2,3,4,5-tetrahydrobenzo[b]azepine-1-carbonyl)benzylcarbamoyl]-2-oxo-2,3,4,5-tetrahydrobenzo[b][1,4]diazepin-1-yl}acetic acid;
4-(3-Aminopropyl)-8-fluoro-3-oxo-3,4-dihydro-2H-quinoxaline-1-carboxylic acid 2-methyl-4-(2,3,4,5-tetrahydrobenzo[b]azepine-1-carbonyl)benzylamide;
4-Cyanomethyl-8-fluoro-3-oxo-3,4-dihydro-2H-quinoxaline-1-carboxylic acid 2-methyl-4-(2,3,4,5-tetrahydrobenzo[b]azepine-1-carbonyl)benzylamide;
4-Cyanomethyl-8-fluoro-3-oxo-3,4-dihydro-2H-quinoxaline-1-carboxylic acid 4-(5H,11H-benzo[e]pyrrolo[1,2-a][1,4]diazepine-10-carbonyl)-2-methylbenzylamide;
7,8-Difluoro-4-(2-hydroxyethyl)-3-oxo-3,4-dihydro-2H-quinoxaline-1-carboxylic acid 2-methyl-4-(2,3,4,5-tetrahydrobenzo[b]azepine-1-carbonyl)benzylamide;
7,8-Difluoro-4-(2-hydroxyethyl)-3-oxo-3,4-dihydro-2H-quinoxaline-1-carboxylic acid 4-(5H,11H-benzo[e]pyrrolo[1,2-a][1,4]diazepine-10-carbonyl)-2-methylbenzylamide;
8-Chloro-4-(2-hydroxyethyl)-3-oxo-3,4-dihydro-2H-quinoxaline-1-carboxylic acid 2-methyl-4-(2,3,4,5-tetrahydrobenzo[b]azepine-1-carbonyl)benzylamide;
8-Fluoro-3,4-dihydro-2H-quinoline-1-carboxylic acid 4-(5H,11H-benzo[e]pyrrolo[1,2-a][1,4]diazepine-10-carbonyl)-2-methylbenzylamide;
8-Fluoro-3-oxo-3,4-dihydro-2H-quinoxaline-1-carboxylic acid 2-chloro-4-(2,3,4,5-tetrahydrobenzo[b]azepine-1-carbonyl)benzylamide;
8-Fluoro-3-oxo-3,4-dihydro-2H-quinoxaline-1-carboxylic acid 4-(6,7-dihydrodibenzo[b,d]azepine-5-carbonyl)-2-methylbenzylamide;
8-Fluoro-3-oxo-3,4-dihydro-2H-quinoxaline-1-carboxylic acid 4-[5-(2-hydroxyethyl)-2,3,4,5-tetrahydrobenzo[b][1,4]diazepine-1-carbonyl]-2-methylbenzylamide;
8-Fluoro-3-oxo-4-(1H-tetrazol-5-ylmethyl)-3,4-dihydro-2H-quinoxaline-1-carboxylic acid 2-methyl-4-(2,3,4,5-tetrahydrobenzo[b]azepine-1-carbonyl)benzylamide;
8-Fluoro-3-oxo-4-(2-oxoethyl)-3,4-dihydro-2H-quinoxaline-1-carboxylic acid 2-methyl-4-(2,3,4,5-tetrahydrobenzo[b]azepine-1-carbonyl)benzylamide;
8-Fluoro-4-(2-hydroxyethyl)-3-oxo-3,4-dihydro-2H-quinoxaline-1-carboxylic acid 2-methyl-4-(2,3,4,5-tetrahydrobenzo[b]azepine-1-carbonyl)benzylamide;
8-Fluoro-4-(2-hydroxyethyl)-3-oxo-3,4-dihydro-2H-quinoxaline-1-carboxylic acid 4-(5H,11H-benzo[e]pyrrolo[1,2-a][1,4]diazepine-10-carbonyl)-2-methylbenzylamide;
8-Fluoro-4-(2-hydroxyethyl)-3-oxo-3,4-dihydro-2H-quinoxaline-1-carboxylic acid 4-(7,8-dihydro-6H-5-oxa-9-azabenzocycloheptene-9-carbonyl)-2-methylbenzylamide;
8-Fluoro-4-(2-methoxyethyl)-3-oxo-3,4-dihydro-2H-quinoxaline-1-carboxylic acid 4-(5H,11H-benzo[e]pyrrolo[1,2-a][1,4]diazepine-10-carbonyl)-2-methylbenzylamide;
8-Fluoro-4-(2-methylaminoethyl)-3-oxo-3,4-dihydro-2H-quinoxaline-1-carboxylic acid 2-methyl-4-(2,3,4,5-tetrahydrobenzo[b]azepine-1-carbonyl)benzylamide;
8-Fluoro-4-methyl-3-oxo-3,4-dihydro-2H-quinoxaline-1-carboxylic acid 2-methyl-4-(4H,10H-3,3a,9-triaza-benzo[f]azulene-9-carbonyl)benzylamide;
8-Fluoro-4-methyl-3-oxo-3,4-dihydro-2H-quinoxaline-1-carboxylic acid 4-(5H,11H-benzo[e]pyrrolo[1,2-a][1,4]diazepine-10-carbonyl)-2-methylbenzylamide;
9-Fluoro-5-(2-hydroxyethyl)-4-oxo-2,3,4,5-tetrahydrobenzo[b][1,4]diazepine-1-carboxylic acid 2-methyl-4-(2,3,4,5-tetrahydrobenzo[b]azepine-1-carbonyl)benzylamide;
9-Fluoro-5-oxo-2,3-dihydro-5H-benzo[e][1,4]oxazepine-1-carboxylic acid 2-methyl-4-(2,3,4,5-tetrahydrobenzo[b]azepine-1-carbonyl)benzylamide;
9-Fluoro-5-oxo-2,3,4,5-tetrahydrobenzo[e][1,4]diazepine-1-carboxylic acid 2-methyl-4-(2,3,4,5-tetrahydrobenzo[b]azepine-1-carbonyl)benzylamide;
8-Fluoro-4-(2-hydroxyethyl)-3-oxo-3,4-dihydro-2H-quinoxaline-1-carboxylic acid 4-[(2-furan-2-ylphenyl)methylcarbamoyl]-2-methylbenzylamide; and
8-Fluoro-4-(2-hydroxyethyl)-3-oxo-3,4-dihydro-2H-quinoxaline-1-carboxylic acid 2-methyl-4-[methyl-(2-thiophen-2-ylphenyl)carbamoyl]benzylamide.

The particularly preferred compounds are V2 agonists of high activity.

The compounds according to the invention are non-peptidic small molecules. It is well known that such compounds have significantly more potential to be orally active than peptides. As such they offer more convenience and better patient compliance than peptidic entities. Additionally, they are easily synthesized.

According to an aspect, the invention concerns a pharmaceutical composition comprising a compound according to the invention as an active agent.

The invention is further related to pharmaceutical compositions incorporating a compound according to the invention used as a vasopressin agonist, which compositions are particularly useful in the treatment of central diabetes insipidus, nocturnal enuresis and nocturia.

According to an aspect of the invention the pharmaceutical composition is for the treatment of polyuria, control of urinary incontinence, voiding postponement, or treatment of bleeding disorders.

The pharmaceutical composition may also include a second pharmacological agent such as a spasmolytic or a potassium channel blocker, these agents being known in the art to ameliorate bladder dysfunction. Preferably, the composition includes only one active constituent. The composition will include excipients selected from binding agents, bulking agents, dispersants, solvents, stabilising agents and the like, such excipients being generally known in the art.

Any excipients used will depend on the intended nature of the formulation, which will, in turn, depend on the intended route of administration. Administration may be oral, transmucosal (such as sublingual, buccal, intranasal, vaginal and rectal), transdermal or by injection (such as subcutaneous, intramuscular and intravenous). Oral administration is generally preferred. For oral administration, the formulation will be a tablet, a capsule or a sachet. Other formulations include dry powders, solutions, suspensions, suppositories and the like.

According to an aspect, the invention concerns the use of a compound of the invention for the manufacture of a medicament for the treatment of a disease selected among nocturnal enuresis, nocturia, polyuria resulting from central diabetes insipidus, urinary incontinence and bleeding disorders.

The compounds according to the present invention are useful for treatment of several diseases, disorders or conditions. The term "treatment" used herein relates to both treatment in order to cure or alleviate a disease, disorder or a condition, and to treatment in order to prevent the development of a disease, disorder or a condition. The treatment may either be performed in an acute or in a chronic way. The human or animal to be treated, i.e. the patient, may be any human or non-human mammal in need of treatment according to the invention.

In a further aspect, the present invention is a method of treating or controlling certain human physiological dysfunctions. This method comprises the administration to the person in need of such treatment of an effective amount of a pharmaceutical composition, which composition contains a compound according to the foregoing description as an active constituent. The compounds act to reduce urine output, and so the method of the invention can be applied to all conditions in which elevated urine output is a contributory factor. The compounds also increase the production of the blood coagulation proteins known as Factor VIII and von Willebrand factor, and so the treatment of bleeding disorders can be undertaken.

In a preferred embodiment, the condition treated is central diabetes insipidus. This is a condition caused by an inability of the body to produce and secrete physiologically active vasopressin, with the result that water re-uptake is greatly reduced and large volumes of urine are produced.

In another preferred embodiment, the condition treated is nocturnal enuresis. This is defined as bladder emptying while the individual is sleeping. It is a condition that mainly affects children and a number of factors may be involved in its etiology.

In another preferred embodiment, the condition treated is nocturia. This is defined as production of sufficient urine during the night to require the individual to wake and empty his (or her) bladder. Again, this condition may be the result of a number of factors.

In another preferred embodiment, the condition treated is incontinence. This condition is characterised, in part, by reduced bladder capacity and control such that involuntary urination occurs unless the bladder is emptied frequently. Incontinence has been divided into two conditions, stress incontinence and urge incontinence. A number of etiological factors are thought to be involved. Treatment according to the invention is particularly useful for delaying the need for bladder emptying ("voiding postponement") in order to allow the incontinent subject a dry period of a few hours (such as up to four hours). Such voiding postponement may also be useful for the non-incontinent population, for example for people obliged to remain in meetings for extended periods.

In another preferred embodiment, the condition treated is haemophilia A or von Willebrand's disease. This is a condition in which Factor VIII or von Willebrand factor production is reduced and the individual suffers from prolonged bleeding.

In another preferred embodiment, the composition is administered prior to surgery (including dental surgery) to increase the coagulability of the blood and so reduce perioperative blood loss.

The administration of the compositions of the present invention will generally be under the control of a physician. The physician will determine the amount of composition to be administered and the dosing schedule, taking into account the patient's physical condition and the therapeutic goals. For an adult diabetes insipidus patient, a typical dose might be between 50 mg and 1 g of the active compound per day, taken as a single tablet or as up to four tablets throughout the day. For routes of administration other than the oral route, the amount of compound will be reduced, since non-oral routes tend to be more efficient in terms of delivering therapeutic agents into the systemic circulation. For the treatment of von Willebrand's disease and haemophilia A, the amount of compound may need to be higher than for the treatment of diabetes insipidus.

Further aspects of the invention relates to methods of treatment of the above mentioned diseases, disorders or conditions. According to a method according to the invention a therapeutically effective amount of the compound, or of the pharmaceutical composition described above, is administered to a patient in need of this treatment. According to different aspects of the invention, it concerns a method of treatment of a disorder selected among nocturnal enuresis, nocturia, diabetes insipidus, urinary incontinence and bleeding disorders, comprising the administration to a person in need of such treatment of an effective amount of a compound according to the invention. According to a preferred aspect, the invention concerns a method for the control of urinary incontinence, wherein the treatment results in voiding postponement.

The term "therapeutically effective amount" relates to an amount that will lead to the desired therapeutical effect. The therapeutically effective amount will be determined by the attending physician taking into consideration all appropriate factors. Generally a single dose will comprise between 0.1 mg and 1000 mg, preferably between 1 mg and 250 mg, of the active compound according to the invention. The dose may be given on a single occasion or repeatedly. When given repeatedly, it may be given at regular intervals, such as once, twice or three times daily, or on demand, according to the condition being treated.

The pharmaceutical composition according to the present invention may be presented in any form that is known in the art. For example, the formulation may be presented as a tablet, capsule, powder, suppository, cream, solution or suspension, or in a more complex form such as an adhesive patch. The formulation will generally include one or more excipients, such as diluents, bulking agents, binding agents, dispersants, solvents, preservatives, flavouring agents and the like. Where the formulation is presented as a tablet or capsule the excipients may optionally include one or more agents to control the release of the active species, such as a coating of a polymer that is insoluble at low pH but soluble at neutral or high pH. Such a coating (known as an "enteric coating") prevents the release of the active agent in the stomach but allows its release in the intestines. The formulation may also include one or more additional pharmacologically active species. Preferably the formulation includes no such additional active agents.

When used as therapeutic agents, the compositions of the present invention may be administered by any appropriate route that is known in the art. For example, they may be administered by the oral, buccal, sublingual, rectal, intravaginal, nasal, pulmonary or transdermal routes. Alternatively, they may be given by injection, including intravenous, subcutaneous and intramuscular injection.

The compounds of the present invention can be prepared by standard chemical manipulations. Such manipulations are e.g. described in EP application 03003394.8 p. 14, 1. 32-p. 20,1. 31 and WO 03/016316 p. 12-17.

In general, compounds according to general formula 1, can be considered to consist of three component parts:
Component $C^1$ corresponding to $G^1$
Component $C^2$ corresponding to the substituted benzoyl unit
Component $C^3$ corresponding to the fused bicyclic unit

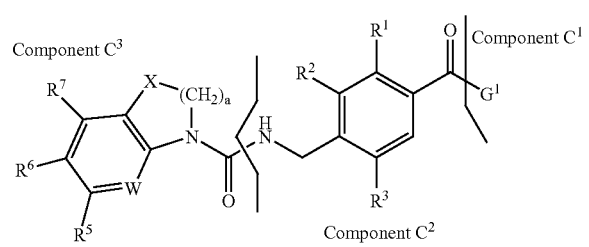

Intermediates corresponding to these components are prepared and then assembled to give the final product. These three components are:
(i) for $C^1$, an amine preferably a $G^1$—H secondary or primary amine
(ii) for $C^2$, a substituted benzoic acid

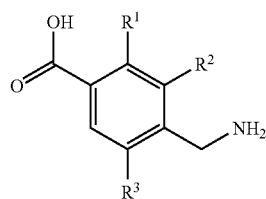

(iii) for $C^3$, a fused bicyclic secondary amine

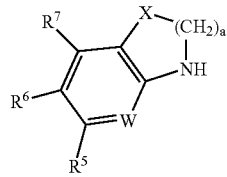

It will be recognised that the substituted benzoic acid for $C^2$ has two functional groups that will need temporary protection during the assembly of the final compound. The principles of functional group protection are well known in the art and are described in, for example, J. F. W. McOmie, "Protective Groups in Organic Chemistry", Plenum Press, 1973; T. W. Greene and P. G. M. Wuts, "Protective Groups in Organic Synthesis", $2^{nd}$ edition, John Wiley, 1991; and P. J. Kocienski, "Protecting groups", Georg Thieme Verlag, 1994. The carboxylic acid group will usually be protected as an ester, such as the methyl, benzyl or tert-butyl ester. The primary amine will usually be protected as a carbamate derivative such as the tert-butyl carbamate (BOC derivative), the benzyl carbamate (CBZ or more simply Z derivative) or the 9-fluorenylmethyl carbamate (Fmoc derivative). Other functional groups may require protection. For example, the group X may include one or more primary or secondary amino groups which may need protection. In the following general description of the synthetic methodology it will be assumed that such protection is used when necessary.

(i) Preparation of Amine for $C^1$

Secondary amines corresponding to $C^1$ where $G^1$ is a group according to general formulae 2-9 are generally not commercially available. They can be prepared according to published methods, or by obvious modifications of such methods. Particularly relevant leading references include the following: Aranapakam et al., Bioorg. Med. Chem. Lett. 1993, 1733; Artico et al., Farmaco. Ed. Sci. 24, 1969, 276; Artico et al., Farmaco. Ed. Sci. 32, 1977, 339; Chakrabarti et al., J. Med. Chem. 23, 1980, 878; Chakrabarti et al., J. Med. Chem. 23, 1980, 884; Chakrabarti et al., J. Med. Chem. 32, 1989, 2573; Chimirri et al., Heterocycles 36, 1993, 601; Grunewald et al., J. Med. Chem. 39, 1996, 3539; Klunder et al., J. Med. Chem. 35, 1992, 1887; Liegéois et al., J. Med. Chem. 37, 1994, 519; Olagbemiro et al., J. Het. Chem. 19, 1982, 1501; Wright et al., J. Med. Chem. 23, 1980, 462; Yamamoto et al., Tet. Lett. 24, 1983, 4711; and International patent application, publication number WO99/06403. Where $G^1$ is a group according to general formula 10 it may be prepared according to published methods or obvious modifications thereof. In particular, a procedure known as the Suzuki reaction may be used which is well described in the literature, one particular reference being Hao et al., Hecheng Huaxue 8(4), 2000, 335-338.

(ii) Preparation of Substituted Benzoic Acid for $C^2$

Substituted benzoic acids corresponding to $C^2$ are not generally items of commerce, but they can be prepared using published methods or obvious variations of such methods.

(iii) Preparation of Fused Bicyclic Secondary Amine for $C^3$

Some of the fused bicyclic secondary amines corresponding to $C^3$ are commercially available. Those that are not can be prepared according to published methods or by obvious modifications of such methods. Particularly relevant leading references include the following: Keller et al., Polyhedron (1983), 2(7), 595-602; Bradley et al., Journal of the Chemical Society, Perkin Transactions 1: Organic and Bio-Organic Chemistry (1972-1999) (1972), (16), 2019-23; Hoenel et al., Journal of the Chemical Society, Perkin Transactions 1: Organic and Bio-Organic Chemistry (1972-1999) (1980), (9), 1933-9. Jacobsen et al., Journal of Medicinal Chemistry (1996), 39(1), 158-75.

With the three components, suitably protected if necessary, in hand, the assembly of the final compound requires the formation of two bonds: between $C^1$ and $C^2$ and between $C^2$ and $C^3$. These bond-forming steps may be taken in any order. Thus, the following sequences can be proposed:

$$C^1+C^2 \rightarrow C^1C^2 \rightarrow C^1C^2C^3$$

$$C^2+C^3 \rightarrow C^2C^3 \rightarrow C^1C^2C^3$$

(i) Formation of $C^1$-$C^2$ Bond

The bond between $C^1$ and $C^2$ is a simple amide bond. The chemistry for making such bonds from a carboxylic acid and a secondary or primary amine is well known in the art of organic synthesis, and particularly in the field of peptide synthesis. The carboxylic acid may be converted into a more reactive species such as an acid chloride (using, for example oxalyl chloride or thionyl chloride) or a mixed anhydride (using isobutyl chloroformate). This reactive species is then added to the secondary or primary amine in a suitable solvent, generally an aprotic solvent such as dichloromethane or dimethylformamide, in the presence of a base such as triethylamine or 4-dimethylaminopyridine, and the reaction is allowed to proceed at a temperature between −20° C. and the boiling point of the solvent. The choice of temperature and the time allowed for the reaction will depend on the reactivity of the two components.

Alternatively, the carboxylic acid and the secondary amine may be mixed in a suitable solvent as above, optionally in the presence of a base, and a condensing agent added. Suitable condensing agents include carbodiimides, such as dicyclohexylcarbodiimide (DCC) and N-ethyl-N'-dimethylaminopropylcarbodiimide (EDC, also WSCDI for water-soluble carbodiimide), phosphorus reagents such as (benzotriazol-1-yloxy)-tris(dimethylamino)phosphonium hexafluorophosphate (BOP), (benzotriazol-1-yloxy)tripyrrolidinophosphonium hexafluorophosphate (PyBOP®) and bromotripyrrolidinophosphonium hexafluorophosphate (PyBroP®), and ureas such as O-(benzotriazol-1-yl)-N,N,N',N'-tetramethyluronium hexafluorophosphate (HBTU).

(ii) Formation of $C^2$-$C^3$ Bond

The bond between $C^2$ and $C^3$ is an urea. The first step in the formation of this bond is generally to react the fused bicyclic amine derivative with phosgene or a phosgene equivalent such as trichloromethyl chloroformate, bis(trichloromethyl) carbonate or carbonyldiimidazole. Again, an aprotic solvent and a tertiary amine base will generally be used. The intermediate formed in this step is usually not isolated. The amine is added and the reaction is allowed to continue, directly forming the carbamate or urea. As an alternative, the reactive intermediate may be formed by the reaction of $C^2$ with the phosgene equivalent and the fused nicyclic amine added in the second part of the synthesis.

The present invention is further illustrated in the following examples, which are intended to demonstrate the application of the invention but not to limit the scope thereof.

EXAMPLES

Abbreviations

| The following abbreviations have been used. | |
|---|---|
| AIBN | Azo-bis-(isobutyronitrile) |
| BOC | tert-Butyloxycarbonyl |
| (BOC)$_2$O | Di-tert-butyl dicarbonate |
| DMF | Dimethylformamide |
| EtOAc | Ethyl acetate |
| IPA | Isopropanol |
| M.S. | Mass spectrometry |
| NBS | N-Bromosuccinimide |
| pet. ether | petroleum ether, fraction boiling at 60-80° C. |
| THF | Tetrahydrofuran |
| WSCDI | Water-soluble carbodiimide |

Preparation of Intermediates

Reagents corresponding to fragment $G^1$ were commercially available or prepared according to the published procedures except where detailed in the specific Examples.

Examples A to G describe the synthesis of intermediates. Compounds according to the present invention are described in Examples 1 to 219.

Example A 4-(tert-Butyloxycarbonylaminomethyl)-3-chlorobenzoic Acid

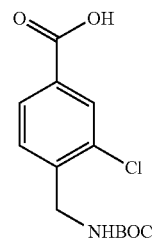

A1. Methyl 4-bromomethyl-3-chlorobenzoate

To a solution of methyl 3-chloro-4-methylbenzoate (5.0 g, 27.1 mmol) in carbon tetrachloride (50 ml) were added NBS (5.8 g, 32.0 mmol) and AIBN (0.442 g, 2.70 mmol). The mixture was stirred at reflux for 18 h. The mixture was allowed to cool to room temperature and then concentrated in vacuo. The residue was purified by flash chromatography on silica (eluant EtOAc:pet. ether 0:100 to 5:95); yield 5.96 g (84%).

A2. 4-(tert-Butyloxycarbonylaminomethyl)-3-chlorobenzoic Acid

To a saturated solution of ammonia in ethanol (170 ml) was added methyl 4-bromomethyl-3-chlorobenzoate from Example A1 (5.5 g, 20.9 mmol). The mixture was stirred at room temperature for 1 hr and then concentrated in vacuo. The residue was triturated with diethyl ether and the resultant white crystals were filtered off and washed with more diethyl ether. To a solution of this solid in water (100 ml) were added solutions of (BOC)$_2$O (5.0 g, 23.0 mmol) in dioxan (100 ml) and sodium hydroxide (1.86 g, 46.0 mmol) in water (100 ml). The mixture was stirred at room temperature for 18 h and then concentrated in vacuo. The aqueous residue was acidified with citric acid and extracted with chloroform/IPA. The organic layer was washed with water, dried over MgSO$_4$, and concentrated in vacuo to give a white solid; yield 2.8 g (67%).

Example B

5-Fluoro-3,4-dihydro-1H-quinoxalin-2-one

B1. 1,2-Difluoro-3-nitrobenzene

To a solution of 2,3-difluoroaniline (5.0 g, 38 mmol) in aqueous tetrafluoroboric acid (48%, 18 ml) was added sodium nitrite (3.9 g, 57 mmol) over 20 min while cooling in an ice/salt bath. After 1 h the mixture was filtered and washed successively with aqueous tetrafluoroboric acid and a mixture of acetone/diethyl ether (40:60). The precipitate was added to a mixture of copper (8.0 g, 121 mmol) and sodium nitrite (39 g, 570 mmol) in water (90 ml) over 20 min. After 1 h the mixture was acidified with concentrated sulphuric acid, extracted with ethyl acetate and evaporated in vacuo. The residue was purified by flash chromatography on silica (eluant EtOAc:pet. ether 20:80); yield 1.4 g (25%).

B2. (2-Fluoro-6-nitrophenylamino)acetic Acid Ethyl Ester

To a solution of 1,2-difluoro-3-nitrobenzene from Example B1 (1.9 g, 12 mmol) in acetonitrile (75 ml) were added glycine ethyl ester hydrochloride (1.7 g, 12 mmol), potassium fluoride (1.2 g, 20 mmol), 18-crown-6 (309 mg, 1.2 mmol) and diisopropylethylamine (4.6 ml, 26 mmol). The mixture was stirred at reflux for 3 h, cooled and evaporated in vacuo. The residue was partitioned between water and EtOAc. The organic layer was washed with brine, filtered and evaporated in vacuo. The residue was purified by flash chromatography on silica (eluant EtOAc:pet. ether 20:80); yield 2.1 g, 73%.

B3. 5-Fluoro-3,4-dihydro-1H-quinoxalin-2-one

To a degassed solution of (2-fluoro-6-nitrophenylamino) acetic acid ethyl ester from Example B2 (2.1 g, 8.7 mmol) in methanol (65 ml) was added palladium on carbon (10%, 600 mg). Hydrogen gas was bubbled through the mixture for 75 mins, filtered through Celite® and reduced in vacuo. The residues was purified by flash chromatography on silica (eluant EtOAc: pet. ether 50:50); yield 1.02 g, 71%.

Example C

4-Cyano-3-methylbenzoic Acid

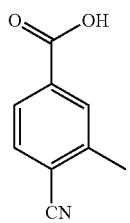

To a solution of 4-bromo-2-methylbenzonitrile (2.0 g, 10.2 mmol) in THF (100 ml) at −78° C. under a nitrogen atmosphere was added dropwise a 2.5M solution of n-butyl lithium (4.48 ml, 11.2 mmol). The mixture was stirred at −78° C. for 1 h and then poured onto solid carbon dioxide (5 g) in THF (50 ml). The mixture was allowed to warm to room temperature. Water was added (200 ml) and the mixture was extracted with diethyl ether (3 times). The aqueous layer was acidified by addition of concentrated HCl and extracted with chloroform (3 times). The combined chloroform extracts were washed with water, dried over MgSO$_4$, and concentrated in vacuo to give a white solid; yield 1.2 g (73%).

Example D

4-Cyano-2-methylbenzoic Acid

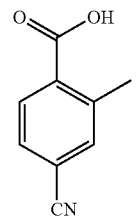

4-Bromo-3-methylbenzonitrile (2.0 g, 10.2 mmol) was reacted following the method of Example C to give a yellow solid which was triturated with hexane and filtered off; yield 0.96 g (59%).

Example E

4-(tert-Butyloxcarbonylaminomethyl)-2-fluorobenzoic Acid

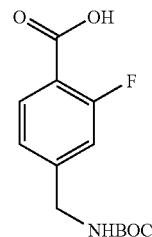

E1. 2-Fluoro-4-methylbenzoic Acid

4-Bromo-3-fluorotoluene (8.33 g, 44.07 mmol) was reacted following the method of Example C to give a white solid; 4.89 g (72%).

E2. Methyl 2-fluoro-4-methylbenzoate

To a solution of 2-fluoro-4-methylbenzoic acid from Example E1 (6.04 g, 39.18 mmol) in toluene (80 ml) was added thionyl chloride (65 ml, 89.11 mmol). The mixture was heated at reflux for 2.5 h, cooled and concentrated in vacuo. The residue was dissolved in dichloromethane (50 ml) and methanol (50 ml) was added. The mixture was stirred at room temperature for 2.5 h and then concentrated in vacuo. The residue was dissolved in dichloromethane (100 ml), washed with saturated sodium bicarbonate solution and brine, dried over MgSO$_4$, and concentrated in vacuo to give a tan solid; yield 5.07 g (77%).

E3. Methyl 4-bromomethyl-2-fluorobenzoate

Methyl 2-fluoro-4-methylbenzoate from Example E2 (5.07 g, 30.16 mmol) was reacted following the method of Example of A1. The product was purified by flash chromatography on silica (eluant EtOAc:pet. ether 20:80); yield 5.9 g (80%).

E4. 4-(tert-Butyloxycarbonylaminomethyl)-2-fluorobenzoic Acid

Methyl 4-brompmethyl-2-fluorobenzoate from Example E3 (5.9 g, 24.13 mmol) was reacted following the method of Example A2. The product was recrystallised from dioxan/pet. ether to give white crystals; yield 2.46 g (38%).

Example F (4-Aminomethyl-3-methylphenyl)-(2,3,4,5-tetrahydrobenzo[b]azepin-1-yl)-methanone

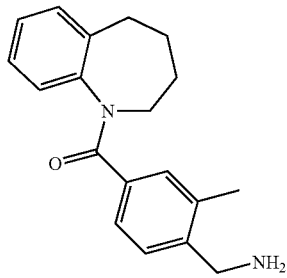

F1. 2-Methyl-4-(2,3,4,5-tetrahydrobenzo[b]azepine-1-carbonyl)benzonitrile

To a solution of 2,3,4,5-tetrahydro-1H-1-benzazepine (0.80 g, 5.4 mmol) in dichloromethane (40 ml) were added 4-cyano-3-methylbenzoic acid from Example C (0.96 g, 6.0 mmol), triethylamine (0.75 ml, 5.4 mmol), 4-dimethylaminopyridine (0.66 g, 5.4 mmol) and WSCDI (2.2 g, 11 mmol). The mixture was stirred at reflux for 18 h, cooled and evaporated in vacuo. The residue was partitioned between EtOAc and 1M KHSO$_4$. The organic layer was washed with saturated sodium bicarbonate solution and brine, dried over MgSO$_4$ and concentrated in vacuo. The residue was purified by flash chromatography on silica (eluant EtOAc:pet. ether 30:70); yield 1.1 g, 70%.

F2. (4-Aminomethyl-3-methylphenyl)-(2,3,4,5-tetrahydrobenzo[b]azepin-1-yl)methanone To a solution of 2-methyl-4-(2,3,4,5-tetrahydrobenzo[b]azepine-1-carbonyl)benzonitrile from Example F1 (430 mg, 1.48 mmol) in methanol (25 ml) was added cobalt (II) chloride (710 mg, 3.0 mmol) and cooled in an ice/water bath. Sodium borohydride (570 mg, 15 mmol) was added portionwise and the mixture was stirred at room temperature for 1 h. The mixture was evaporated, 1N HCl(aq) (20 ml) was added and stirred for 15 mins. The mixture was filtered through Celite® and the Celite® was washed with 2-propanol:chloroform, 20:80 (100 ml). The mixture was separated and the aqueous layer washed with diethyl ether. The aqueous layer was basified with 2N NaOH(aq), chloroform was added and the mixture filtered through Celite®. The Celite® was washed with chloroform. The mixture was separated and the organic layer dried and evaporated, yield 340 mg, 78%.

Example G (4-Aminomethyl-3-methylphenyl)-(5H,11H-benzo[e]pyrrolo[1,2-a][1,4]diazepin-10-yl)methanone

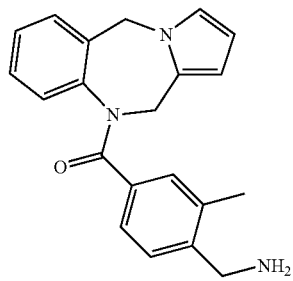

G1. 4-(5H,11H-Benzo[e]pyrrolo[1,2-a][1,4]diazepine-10-carbonyl)-2-methylbenzonitrile A solution of 4-cyano-3-methylbenzoic acid from Example C (1.2 g, 7.5 mmol) and thionyl chloride (3.6 ml, 54 mmol) in toluene (20 ml) was heated at reflux for 2 h. The mixture was evaporated and azeotroped with toluene. The residue was dissolved in dichloromethane, 10,11-dihydro-5H-benzo[e]pyrrolo[1,2-a][1,4]diazepine (1.4 g, 7.5 mmol) was added and the mixture stirred for 18 h. The mixture was evaporated and the residue purified by flash chromatography on silica (EtOAc:pet ether, 30:70 to 80:20) to give a cream solid, yield 1.5 g, 63%.

G2. (4-Aminomethyl-3-methylphenyl)-(5H,11H-benzo[e]pyrrolo[1,2-a][1,4]diazepin-10-yl)methanone Following a similar procedure as described for Example F2, 4-(5H,11H-benzo[e]pyrrolo[1,2-a][1,4]diazepine-10-carbonyl)-2-methylbenzonitrile from Example G1 (1.5 g, 4.6 mmol) was treated with cobalt (II) chloride (2.2 g, 9.2 mmol) and sodium borohydride (1.75 g, 46 mmol) to afford a pale yellow solid, yield 680 mg, 44%.

Example 1

{6-Fluoro-5-[2-methyl-4-(2,3,4,5-tetrahydrobenzo[b]azepine-1-carbonyl)-benzylcarbamoyl]-2-oxo-2,3,4,5-tetrahydrobenzo[b][1,4]diazepin-1-yl}-acetic Acid Tert-Butyl Ester

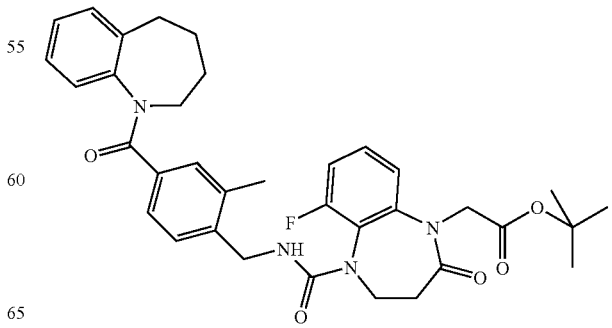

1A. 3-(2-Fluoro-6-nitrophenylamino)propionic Acid Methyl Ester

To a solution of 1,2-difluoro-3-nitrobenzene from Example B1 (500 mg, 3.1 mmol) in acetonitrile (25 ml) were added β-alanine methyl ester hydrochloride (440 mg, 3.1 mmol), potassium fluoride (310 mg, 5.3 mmol), 18-crown-6 (84 mg, 0.3 mmol) and diisopropylethylamine (1.2 ml, 7 mmol). The mixture was stirred at reflux for 2 h, cooled and evaporated in vacuo. The residue was partitioned between water and EtOAc. The organic layer was washed with brine, filtered and evaporated in vacuo. The residue was purified by flash chromatography on silica (eluant EtOAc:pet. ether 25:75); yield 650 mg, 86%.

1B. 6-Fluoro-1,3,4,5-tetrahydrobenzo[b][1,4]diazepin-2-one

To a degassed solution of 3-(2-fluoro-6-nitrophenylamino) propionic acid methyl ester from Example 1A (650 mg, 2.7 mmol) in methanol (40 ml) was added palladium on carbon (10%, 200 mg). Hydrogen gas was bubbled through the mixture for two hours, filtered through Celite® and reduced in vacuo. The residue was dissolved in propan-2-ol (20 ml) and to it was added acetic acid (2 ml). The mixture was stirred for 18 h, heated at reflux for 2 h, cooled, reduced in vacuo and azeotroped with toluene; yield 480 mg, 99%.

1C. (6-Fluoro-2-oxo-2,3,4,5-tetrahydrobenzo[b][1,4]diazepin-1-yl)acetic Acid Tert-Butyl Ester To a solution of 6-fluoro-1,3,4,5-tetrahydrobenzo[b][1,4]diazepin-2-one from Example 1B (220 mg, 1.2 mmol) in DMF (4 ml) was added sodium hydride (60%, 48 mg, 1.2 mmol) while cooling in an ice/water bath. The mixture was allowed to warm to room temperature and was stirred for 10 min. Tert-butyl bromoacetate (190 µl, 1.2 mmol) was added and the mixture was stirred for 18 h. Brine was added and the mixture was evaporated in vacuo. The residue was partitioned between EtOAc and brine and the organic layer was reduced in vacuo. The residue was purified by flash chromatography on silica (eluant: EtOAc:pet ether 60:40); yield 240 mg, 67%.

1D. {6-Fluoro-5-[2-methyl-4-(2,3,4,5-tetrahydrobenzo[b]azepine-1-carbonyl)-benzylcarbamoyl]-2-oxo-2,3,4,5-tetrahydrobenzo[b][1,4]diazepin-1-yl}acetic Acid Tert-Butyl Ester To a solution of (6-fluoro-2-oxo-2,3,4,5-tetrahydrobenzo[b][1,4]diazepin-1-yl)-acetic acid tert-butyl ester from Example 1C (240 mg, 0.80 mmol) in THF (8 ml) were added a solution of phosgene in toluene (20%, 0.55 ml, 1.1 mmol) and diisopropylethylamine (190 µl, 1.1 mmol). The mixture was stirred for 2 h. To the mixture were added a solution of (4-aminomethyl-3-methylphenyl)-(2,3,4,5-tetrahydrobenzo[b]azepin-1-yl)methanone from Example F (220 mg, 0.75 mmol) in THF (2 ml) and diisopropylethylamine (190 µl, 1.1 mmol). The mixture was stirred for 18 h and evaporated in vacuo. The residue was purified by flash column chromatography on silica (eluant EtOAc:pet. ether 80:20) to give a white solid; yield 295 mg, 64%.

M.S.: calc m/e—614.72; found [M+H]⁺—615.3

Example 2

{6-Fluoro-5-[2-methyl-4-(2,3,4,5-tetrahydrobenzo[b]azepine-1-carbonyl)-benzylcarbamoyl]-2-oxo-2,3,4,5-tetrahydrobenzo[b][1,4]diazepin-1-yl]-acetic Acid

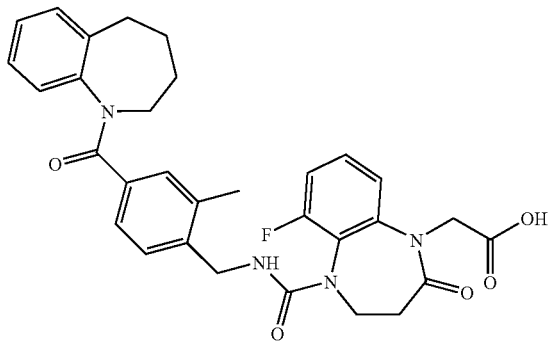

To a solution of {6-fluoro-5-[2-methyl-4-(2,3,4,5-tetrahydrobenzo[b]azepine-1-carbonyl)benzylcabamoyl]-2-oxo-2,3,4,5-tetrahydrobenzo[b][1,4]diazepin-1-yl]acetic acid tert-butyl ester from Example 1 (250 mg, 0.40 mmol) in dichloromethane (8 ml) was added trifluoroacetic acid (8 ml). The mixture was stirred for 90 min and evaporated in vacuo and azeotroped with toluene to give an off-white solid; yield 220 mg, 99%.

M.S.: calc m/e—558.61; found [M+H]⁺—559.2

Example 3

9-Fluoro-5-(2-hydroxyethyl)-4-oxo-2,3,4,5-tetrahydrobenzo[b][1,4]diazepine-1-carboxylic Acid 2-methyl-4-(2,3,4,5-tetrahydrobenzo[b]azepine-1-carbonyl)benzylamide

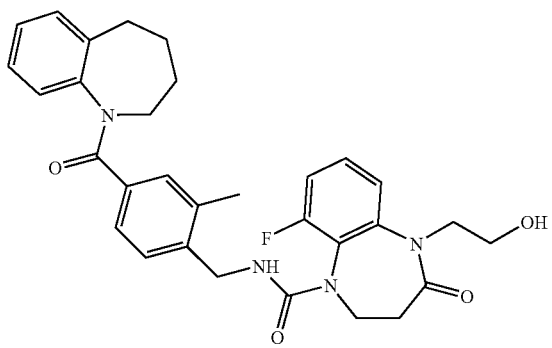

To a solution of {6-fluoro-5-[2-methyl-4-(2,3,4,5-tetrahydrobenzo[b]azepine-1-carbonyl)benzylcarbamoyl]-2-oxo-2,3,4,5-tetrahydrobenzo[b][1,4]diazepin-1-yl}acetic acid from Example 2 (170 mg, 0.30 mmol) in THF (6 ml) were added N-methylmorpholine (47 µl, 0.43 mmol) and isobutyl chloroformate (57 µl, 0.43 mmol) while cooling in an ice/water bath. The mixture was stirred for 1 h, filtered and added to a solution of sodium borohydride (27 mg, 0.70 mmol) in water (1.5 ml) while cooling in an ice/water bath. The mixture was allowed to warm to room temperature slowly and stirred for 2 h. Saturated ammonium chloride solution (2 ml) was added and the mixture evaporated in vacuo. The residue was partitioned between choroform and water and the organic layer was washed with brine, dried over magnesium sulphate and evaporated in vacuo. The residue was purified by flash chromatography on silica (eluant methanol:dichloromethane 6:94) to give a white solid; yield 104 mg, 64%.

M.S.: calc m/e—544.63; found [M+H]⁺—545.2

Example 4

{1-[4-(5H,11H-Benzo[e]pyrrolol[1,2-a][1,4]diazepine-10-carbonyl)-2-methylbenzylcarbamoyl]-8-fluoro-2,3-dihydro-1H-quinolin-4-ylidene}acetic Acid Ethyl Ester

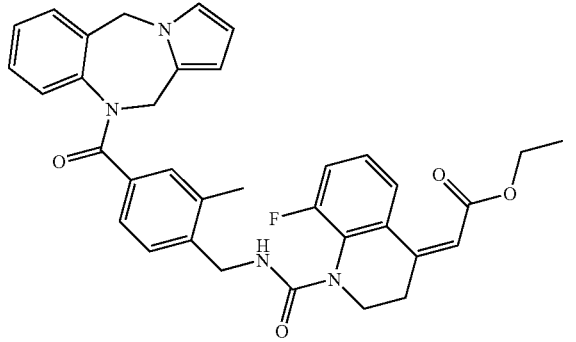

4A. (8-Fluoro-2,3-dihydro-1H-quinolin-4-ylidene)acetic Acid Ethyl Ester

Triethyl phosphonoacetate (480 µl, 2.42 mmol) was added to a suspension of sodium hydride (60%, 97 mg, 2.42 mmol) in THF (5 ml) while cooling in an ice/water bath. After 2 h 8-fluoro-2,3-dihydro-1H-quinolin-4-one was added and the mixture warmed to 50° C. and stirred for 16 h. The mixture was cooled, brine was added and the mixture was evaporated. EtOAc and brine were added to the residue and separated. The organic layer was dried and evaporated and the residue was purified by flash chromatography on silica (eluant pet.ether 100% to pet. ether:EtOAc 90:10) to give a green solid identified as (8-fluoro-2,3-dihydro-1H-quinolin-4-ylidene)acetic acid ethyl ester; yield 50 mg, 18% and a green solid identified as (8-fluoro-1,2-dihydroquinolin-4-yl)-acetic acid ethyl ester; yield 20 mg, 7%.

4B. {1-[4-(5H,11H-Benzo[e]pyrrolo[1,2-a][1,4]diazepine-10-carbonyl)-2-methylbenzylcarbamoyl]-8-fluoro-2,3-dihydro-1H-quinolin-4-ylidene}acetic Acid Ethyl Ester A mixture of (8-fluoro-2,3-dihydro-1H-quinolin-4-ylidene)acetic acid ethyl ester from Example 4A (50 mg, 0.21 mmol), trichloromethyl chloroformate (28 µl, 0.23 mmol), diisopropylethylamine (41 µl, 0.23 mmol) and a small spatula of activated carbon in toluene (2 ml) was heated at reflux for 2 h. After cooling, EtOAc was added and the mixture filtered through Celite® and evaporated. The residue was taken up in THF to which was added a solution of (4-aminomethyl-3-methylphenyl)-(5H,11H-benzo[e]pyrrolo[1,2-a][1,4]diazepin-10-yl)methanone from Example G (77 mg, 0.23 mmol) and diisopropylethylamine (41 µl, 0.23 mmol) in dichloromethane (2 ml). The mixture was stirred for 18 h, evaporated and the residue was purified by flash chromatography on silica (EtOAC:pet ether, 20:80 to 50:50) to give a white solid, yield 4 mg (3%).

M.S.: calc m/e—592.7; found [M+H]⁺—593.2

Example 5

{1-[4-(5H,11H-Benzo[e]pyrrolo[1,2-a][1,4]diazepine-10-carbonyl)-2-methylbenzylcarbamoyl)]-8-fluoro-1,2-dihydroquinolin-4-yl}acetic Acid Ethyl Ester

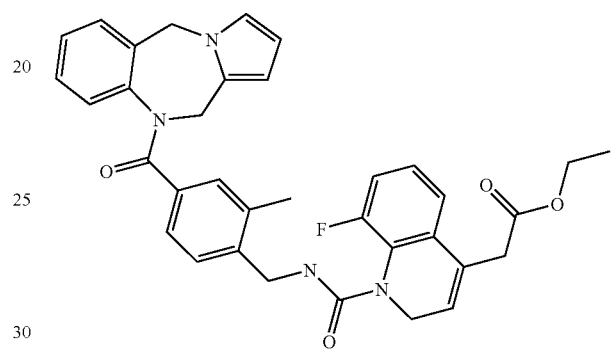

Following a similar procedure as described for Example 4B (8-Fluoro-1,2-dihydroquinolin-4-yl)-acetic acid ethyl ester from Example 4A (20 mg, 0.085 mmol) was reacted with trichloromethyl chloroformate (11 µl, 0.094 mmol) and (4-aminomethyl-3-methylphenyl)-(5H,11H-benzo[e]pyrrolo[1,2-a][1,4]diazepin-10-yl)methanone from Example G (31 mg, 0.094 mmol). Purification on silica (EtOAC:pet ether, 20:80 to 50:50) afforded a white solid, yield 4 mg (8%).

M.S.: calc m/e—592.7; found [M+H]⁺—593.2

Example 6

{1-[4-(5H,11H-Benzo[e]pyrrolo[1,2-a][1,4]diazepine-10-carbonyl)-2-methylbenzylcarbamoyl]-8-fluoro-1,2,3,4-tetrahydroquinolin--4-yl}acetic Acid Ethyl Ester

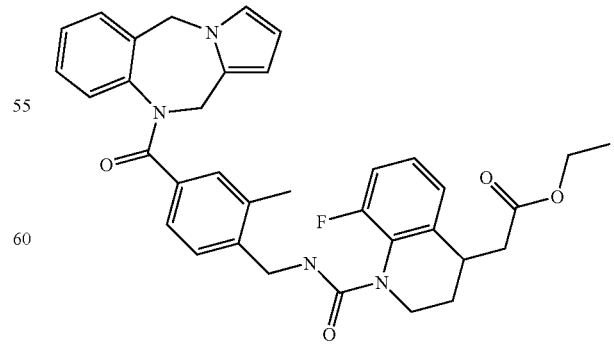

A mixture (75 mg, 0.13 mmol) of {1-[4-(5H,11H-benzo[e]pyrrolo[1,2-a][1,4]diazepine-10-carbonyl)-2-methylbenzylcarbamoyl]-8-fluoro-2,3-dihydro-1H-quinolin-4-ylidene}acetic acid ethyl ester from Example 4 and {1-[4-(5H,11H-benzo[e]pyrrolo[1,2-a][1,4]diazepine-10-carbonyl)-2-methyl-benzylcarbamoyl]-8-fluoro-1,2-dihydroquinolin-4-yl]acetic acid ethyl ester from Example 5 was dissolved in methanol (50 ml). To the solution was added a catalytic amount of 10% palladium on carbon and the mixture was stirred under a hydrogen atmosphere for 6 h. The mixture was filtered through Celite® and evaporated. The mixture was redissolved in methanol (50 ml), a further catalytic amount of 10% palladium on carbon was added and the mixture stirred under a hydrogen atmosphere for 3 h. The mixture was filtered and evaporated to give a white solid, yield 74 mg (97%).

M.S.: calc m/e—594.7; found [M+H]$^+$—595.2

Example 7

{5-Fluoro-4-[2-methyl-4-(2,3,4,5-tetrahydrobenzo[b]azepine-1-carbonyl)-benzylcarbamoyl]-2-oxo-3,4-dihydro-2H-quinoxalin-1-yl}acetic Acid Tert-Butyl Ester

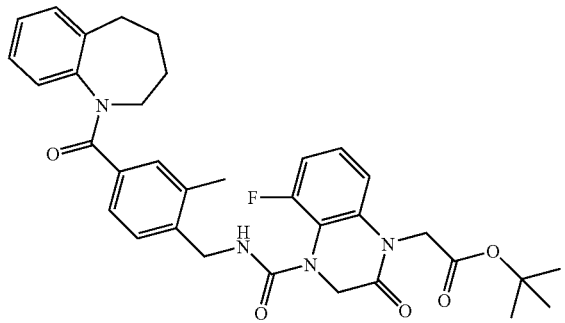

7A. (5-Fluoro-2-oxo-3,4-dihydro-2H-quinoxalin-1-yl)acetic Acid Tert-Butyl Ester

To a solution of 5-fluoro-3,4-dihydro-1H-quinoxalin-2-one from Example B (475 mg, 2.86 mmol) in THF (10 ml) was added sodium hydride (60%, 115 mg, 2.86 mg) while cooling in an ice/water bath. The mixture was allowed to warm to room temperature, stirred for 30 min and cooled in an ice/water bath. tert-Butyl bromoacetate (460 μl, 2.86 mmol) was added and the mixture was allowed to warm to room temperature slowly and stirred for 18 h. Brine was added and the mixture was evaporated in vacuo. The residue was partitioned between brine and EtOAc and the organic layer was dried and evaporated in vacuo. The residue was purified by flash chromatography on silica (eluant EtOAc;pet. ether 40:60) to give a white solid; yield 500 mg, 62%.

7B. {5-Fluoro-4-[2-methyl-4-(2,3,4,5-tetrahydrobenzo[b]azepine-1-carbonyl)-benzylcarbamoyl]-2-oxo-3,4-dihydro-2H-quinoxalin-1-yl}acetic Acid Tert-Butyl Ester To a solution of (5-fluoro-2-oxo-3,4-dihydro-2H-quinoxalin-1-yl)acetic acid tert-butyl ester from Example 7A (84 mg, 0.30 mmol) in toluene (4.0 ml) were added trichloromethyl chloroformate (36 μl, 0.30 mmol), diisopropylethylamine (54 μl, 0.30 mmol) and a spatula full of activated carbon. The mixture was heated at reflux for 2 h, cooled, filtered through Celite®, washed with EtOAc and evaporated in vacuo. The residue was taken up in THF (3.0 ml) and added to a solution of (4-aminomethyl-3-methylphenyl)-(2,3,4,5-tetrahydrobenzo[b]azepin-1-yl)methanone from Example F (85 mg, 0.29 mmol) in THF (3.0 ml) while cooling in an ice/water bath. The mixture was allowed to warm to room temperature, stirred for 1 h and evaporated in vacuo. The residue was purified by flash chromatography on silica (eluant EtOAc:pet. ether 75:25) to afford a white solid; yield 120 mg, 66%.

Example 8

{5-Fluoro-4-[2-methyl-4-(2,3,4,5-tetrahydrobenzo[b]azepine-1-carbonyl)-benzylcarbamoyl]-2-oxo-3,4-dihydro-2H-quinoxalin-1-yl}acetic Acid

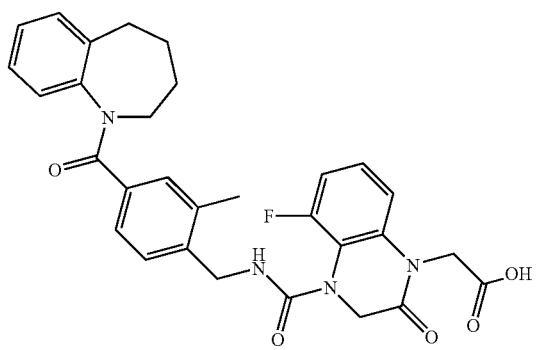

To a solution of {5-fluoro-4-[2-methyl-4-(2,3,4,5-tetrahydrobenzo[b]azepine-1-carbonyl)benzylcarbamoyl]-2-oxo-3,4-dihydro-2H-quinoxalin-1-yl}acetic acid tert-butyl ester from Example 7B (105 mg, 0.175 mmol) in dichloromethane (4.0 ml) was added trifluoroacetic acid (4.0 ml). The mixture was stirred for 1.5 h, evaporated in vacuo and azeotroped with toluene to give a white solid; yield 95 mg, 100%.

Example 9

8-Fluoro-4-(2-hydroxyethyl)-3-oxo-3,4-dihydro-2H-quinoxaline-1-carboxylic Acid 2-methyl-4-(2,3,4,5-tetrahyrobenzo[b]azepine-1-carbonyl)benzylamide

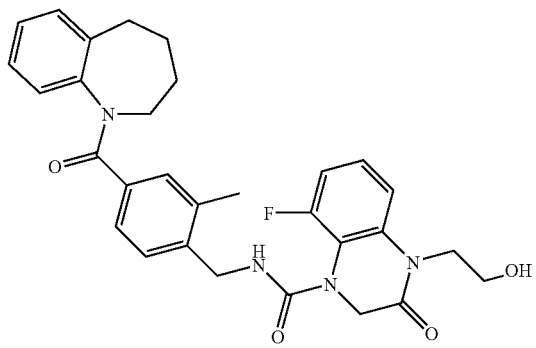

To a solution of {5-fluoro-4-[2-methyl-4-(2,3,4,5-tetrahydrobenzo[b]azepine-1-carbonyl)benzylcarbamoyl]-2-oxo-3,4-dihydro-2H-quinoxalin-1-yl}acetic acid from Example 8 (70 mg, 0.13 mmol) in THF (4.0 ml) was added N-methylmorpholine (18 μl, 0.18 mmol). The solution was cooled in an ice/water bath and isobutyl chloroformate (23 μl, 0.18 mmol) was added. The mixture was stirred in the ice/water bath for 1 h, filtered and added to a solution of sodium borohydride (12 mg, 0.32 mmol) in water (1.0 ml) in an ice/water bath. The mixture was allowed to warm to room temperature slowly and stirred at room temperature for 1 h. Saturated ammonium chloride (1 ml) was added and the mixture was evaporated in vacuo. The residue was taken up in water and extracted with chloroform. The organic phase was washed with brine, dried and evaporated in vacuo to give a white solid; yield 56 mg, 81%.

Example 10

8-Fluoro-3-oxo-4-(2-oxoethyl)-3,4-dihydro-2H-quinoxaline-1-carboxylic Acid 2-methyl-4-(2,3,4,5-tetrahydrobenzo[b]azepine-1-carbonyl)benzylamide

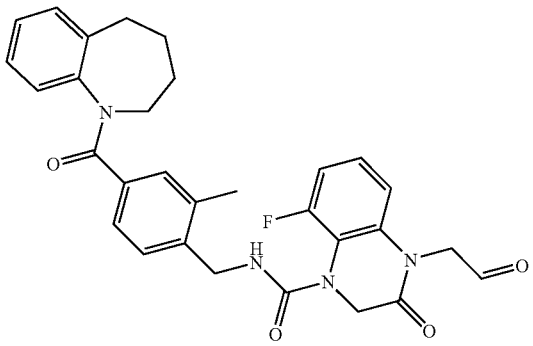

To a solution of 8-fluoro-4-(2-hydroxyethyl)-3-oxo-3,4-dihydro-2H-quinoxaline-1-carboxylic acid 2-methyl-4-(2,3,4,5-tetrahydrobenzo[b]azepine-1-carbonyl)benzylamide from Example 9 (105 mg, 0.20 mmol) in dichloromethane (5 ml) was added Dess-Martin periodinane (100 mg, 0.24 mg). The mixture was stirred for 2 h and evaporated. The residue was taken up in chloroform and water and separated. The organic layer was dried and evaporated. The residue was purified by flash chromatography on silica (eluant methanol:dichloromethane 4:96) to give a white solid; yield 73 mg, 69%.

M.S.: calc m/e—528.59; found [M+H]$^+$—529.4

Example 11

8-Fluoro-4-(2-methylaminoethyl)-3-oxo-3,4-dihydro-2H-quinoxaline-1-carboxylic acid 2-methyl-4-(2,3,4,5-tetrahydrobenzo[b]azepine-1-carbonyl)benzylamide

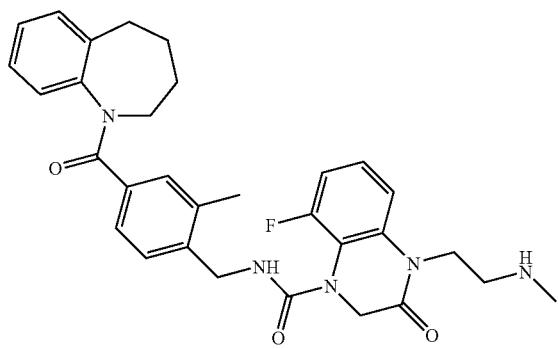

Methylamine hydrochloride (68 mg, 1.0 mmol) was added to a solution of 8-fluoro-3-oxo-4-(2-oxoethyl)-3,4-dihydro-2H-quinoxaline-1-carboxylic acid 2-methyl-4-(2,3,4,5-tetrahydrobenzo[b]azepine-1-carbonyl)benzylamide from Example 10 (53 mg, 0.1 mmol) in methanol (4.0 ml) then the mixture was cooled in an ice/water bath. Diisopropylethylamine (185 µl, 1.0 mmol) was added and the mixture was stirred for 20 mins. Acetic acid (0.40 ml) and sodium cyanoborohydride (6.3 mg, 0.1 mmol) were added and the mixture was allowed to warm to room temperature. The mixture was stirred for 3 h, diluted with toluene and evaporated in vacuo. The residue was partitioned between EtOAc and saturated sodium hydrogen carbonate solution and separated. The organic phase was washed with brine, dried and evaporated in vacuo. The residue was purified by flash chromatography on silica (eluant dichloromethane:methanol:triethylamine 95:4:1) to give a white solid; yield 22 mg, 41%.

M.S.: calc m/e—543.64; found. [M+H]$^+$—544.8

Example 12

{5-Chloro-4-[2-methyl-4-(2,3,4,5-tetrahydrobenzo[b]azepine-1-carbonyl)-benzylcarbamoyl]-2-oxo-3,4-dihydro-2H-quinoxalin-1-yl}acetic Acid Tert-Butyl Ester

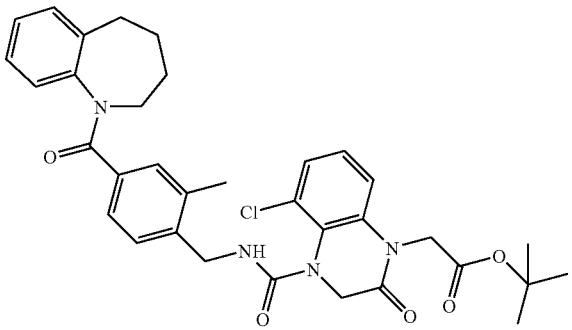

12A. tert-Butyl-(2-chloro-6-nitrophenyl)amine

A mixture of 2,3-dichloronitrobenzene (5 g, 26 mmol), tert-butylamine (7.4 ml, 71 mmol) and ethanol (2.5 ml) was heated at 150° C. in a sealed tube for 3 days. The mixture was evaporated, the residue taken up in EtOAc, washed with water and brine, dried and evaporated to afford a yellow oil; yield 5.3 g, 90%.

12B. N*2*-tert-Butyl-3-chlorobenzene-1,2-diamine

A solution of titanium (III) chloride (10 wt. % in 20-30% hydrochloric acid, 120 ml, 78 mmol) was added drop wise to a solution of tert-butyl-(2-chloro-6-nitrophenyl)-amine from Example 12A (5.7 g, 25 mmol) and sodium acetate (112 g, 1.4 moles) in methanol (205 ml) and water (63 ml). The mixture was stirred for 2 h, water was added to dissolve remaining solids and the organic solvent was evaporated. The mixture was neutralised with solid sodium hydrogen carbonate and extracted with EtOAc. The organic extracts were dried and evaporated to afford an orange oil; yield 4.7 g, 94%.

12C. 4-tert-Butyl-5-chloro-3,4-dihydro-1H-quinoxalin-2-one

Bromoacetyl bromide (2.8 ml, 32 mmol) was added drop wise to a solution of N*2*-tert-butyl-3-chlorobenzene-1,2- diamine from Example 12B (4.1 g, 21 mmol) and diisopropylethylamine (11 ml, 63 mmol) in THF (75 ml) while cooling to −78° C. The mixture was allowed to warm to room temperature over 18 h and the solvent was evaporated. Chloroform was added and the mixture was washed with sodium hydrogen carbonate, dried and evaporated. To the residue were added acetonitrile (90 ml), diisopropylethylamine (5.6 ml, 32 mmol) and sodium iodide (3.2 g, 21 mmol). The mixture was heated at reflux for 18 h, cooled and evaporated. The residue was taken up in chloroform, washed with water, dried and evaporated. The residue was purified by flash chromatography on silica (eluant pet.ether:EtOAc 100:0 to 50:50) to give an orange solid; yield 1.5 g, 29%.

12D. 5-Chloro-3,4-dihydro-1H-quinoxalin-2-one 4-tert-Butyl-5-chloro-3,4-dihydro-1H-quinoxalin-2-one from Example 12C (1.5 g, 6.1 mmol) was suspended in 2N sulphuric acid (45 ml) and stirred for 18 h. The mixture was filtered and the filtrate was neutralised with sodium hydrogen carbonate, extracted with EtOAc, dried and evaporated. The residue was taken up in ethanol (30 ml) and cooled in an ice/water bath. Sodium borohydride (460 mg, 12 mmol) was added and the mixture was allowed to warm to room temperature over 2 h. Water (1 ml) was added and the mixture was evaporated. The residue was triturated with ice-cold water, filtered, washed with ice-cold water and dried in vacuo over phosphorous pentoxide to give an orange solid; yield 550 mg, 49%.

12E. (5-Chloro-2-oxo-3,4-dihydro-2H-quinoxalin-1-yl)acetic Acid Tert-Butyl Ester Following the same procedure as described for Example 1C, 5-chloro-3,4-dihydro-1H-quinoxalin-2-one from Example 12D (350 mg, 1.9 mmol) was reacted with sodium hydride (60%, 84 mg, 2.1 mmol) and tert-butyl bromoacetate (340 µl, 2.1 mmol). The product was purified by flash chromatography on silica (eluant pet. ether:EtOAc 100:0 to 50:50) to give a brown solid; yield 450 mg, 79%.

12F. {5-Chloro-4-[2-methyl-4-(2,3,4,5-tetrahydrobenzo[b]azepine-1-carbonyl)benzylcarbamoyl]-2-oxo-3,4-dihydro-2H-quinoxalin-1-yl}acetic Acid Tert-Butyl Ester Following the same procedure as described for 1D, (5-chloro-2-oxo-3,4-dihydro-2H-quinoxalin-1-yl)acetic acid tert-butyl ester from Example 12E (450 mg, 1.5 mmol) was treated with phosgene (2.0 mmol) and diisopropylethylamine (2.0 mmol) followed by (4-aminomethyl-3-methylphenyl)-(2,3,4,5-tetrahydrobenzo[b]azepin-1-yl)methanone from Example F (450 mg, 1.5 mmol) and diisopropylethylamine (2.0 mmol). The product was purified by flash chromatography on silica (eluant pet.ether:EtOAC, 100:0 to 50:50) to give a pale red solid; yield 510 mg, 54%.

M.S.: calc m/e—617.15; found [M+H]$^+$—617.2 ($^{35}$Cl)

Example 13

4-Cyanomethyl-8-fluoro-3-oxo-3,4-dihydro-2H-quinoxaline-1-carboxylic Acid 2-methyl-4-(2,3,4,5-tetrahydrobenzo[b]azepine-1-carbonyl)-benzylamide

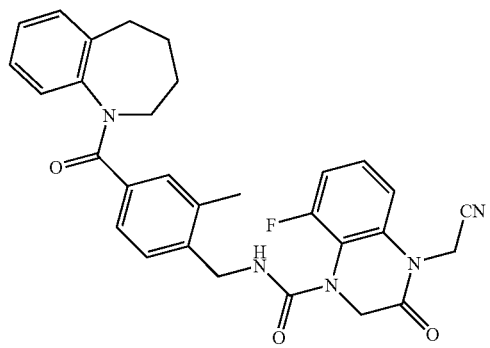

13A. (5-Fluoro-2-oxo-3,4-dihydro-2H-quinoxalin-1-yl)acetonitrile

Sodium hydride (60%, 84 mg, 2.1 mmol) was added to a solution of 5-fluoro-3,4-dihydro-1H-quinoxalin-2-one from Example B (316 mg, 1.9 mmol) in THF (2.0 ml) while cooling in an ice/water bath. The mixture was allowed to warm to room temperature and stirred for 30 mins. Bromoacetonitrile (146 µl, 2.1 mmol) was added and the mixture was stirred for 18 h. Brine was added and the mixture evaporated in vacuo. The residue was portioned between EtOAc and water, separated and the organic phase was dried and evaporated in vacuo. The residue was purified by flash chromatography on silica (eluant 100% pet ether then EtOAc:pet. ether 20:80); yield 183 mg, 47%.

13B. 4-Cyanomethyl-8-fluoro-3-oxo-3,4-dihydro-2H-quinoxaline-1-carboxylic Acid 2-methyl-4-(2,3,4,5-tetrahydrobenzo[b]azepine-1-carbonyl)benzylamide To a solution of (5-fluoro-2-oxo-3,4-dihydro-2H-quinoxalin-1-yl)acetonitrile from Example 13A (183 mg, 0.89 mmol) in THF (2 ml) were added a solution of phosgene in toluene (20%, 0.61 ml, 1.2 mmol) and diisopropylethylamine (200 µl, 1.2 mmol). The mixture was stirred for 2 h. To the mixture were added a solution of (4-aminomethyl-3-methylphenyl)-(2,3,4,5-tetrahydrobenzo[b]azepin-1-yl)methanone from Example F (260 mg, 0.89 mmol) in THF (2 ml) and diisopropylethylamine (155 µl, 0.89 mmol). The mixture was stirred for 2 h and evaporated in vacuo. The residue was purified by flash column chromatography on silica (eluant EtOAc:pet. ether 80:20 to EtOAc 100%) to give a white solid; yield 268 mg, 57%.

M.S.: calc m/e—525.58; found [M+H]$^+$—526.1

Example 14

8-Fluoro-3-oxo-4-(1H-tetrazol-5-ylmethyl)-3,4-dihydro-2H-quinoxaline-1-carboxylic Acid 2-methyl-4-(2,3,4,5-tetrahydrobenzo[b]azepine-1-carbonyl)benzylamide

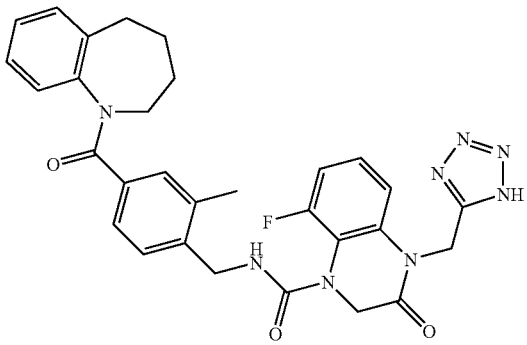

Sodium azide (78 mg, 1.2 mmol) and ammonium chloride (21 mg, 0.40 mmol) were added to a solution of 4-cyanomethyl-8-fluoro-3-oxo-3,4-dihydro-2H-quinoxaline-1-carboxylic acid 2-methyl-4-(2,3,4,5-tetrahydrobenzo[b]azepine-1-carbonyl)benzylamide from Example 13 (210 mg, 0.40 mmol) in DMF (5 ml) and the mixture was stirred at 100° C. for 18 h. The mixture was cooled and evaporated in vacuo. The residue was purified by flash chromatography on silica (eluant CHCl$_3$ 100% to CHCl$_3$:methanol;triethylamine 97:2:1 to CHCl$_3$:methanol;triethylamine 94:4:2). The product was partitioned between chloroform and potassium hydrogen sulphate, separated and the organic phase was dried and evaporated in vacuo; yield 33 mg, 15%.

M.S.: calc m/e—568.61; found [M+H]$^+$—569.1

Example 15

4-(3-Aminopropyl)-8-fluoro-3-oxo-3,4-dihydro-2H-quinoxaline-1-carboxylic Acid 2-methyl-4-(2,3,4,5-tetrahydrobenzo[b]azepine-1-carbonyl)benzylamide

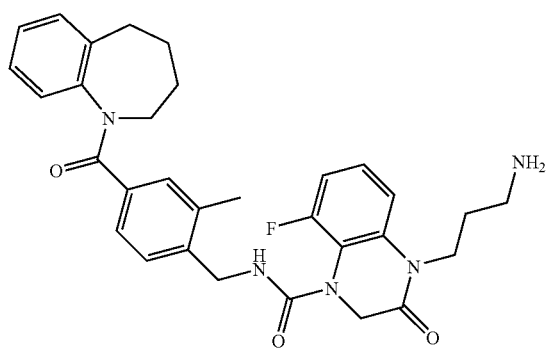

15A. 1-(3-Aminopropyl)-5-fluoro-3,4-dihydro-1H-quinoxalin-2-one

Sodium hydride (60%, 48 mg, 1.2 mmol) was added to a solution of 5-fluoro-3,4-dihydro-1H-quinoxalin-2-one from Example B (200 mg, 1.2 mmol) in DMF (3 ml) while cooling in an ice/water bath. The mixture was allowed to warm to room temperature and stirred for 10 mins. (3-Bromopropyl)carbamic acid tert-butyl ester (290 mg, 1.2 mmol) and sodium iodide (180 mg, 1.2 mmol) were added and the mixture was stirred at room temperature for 18 h. Brine was added and the mixture was evaporated in vacuo. The residue was partitioned between EtOAc and brine, separated and the organic phase was dried and evaporated in vacuo. The residue was purified by flash chromatography on silica (eluant EtOAc:pet. ether 50:50) to give a pale yellow gum; yield 230 mg, 59%.

15B. (3-{5-Fluoro-4-[2-methyl-4-(2,3,4,5-tetrahydrobenzo[b]azepine-1-carbonyl)benzylcarbamoyl]-2-oxo-3,4-dihydro-2H-quinoxalin-1-yl}propyl)carbamic Acid Tert-Butyl Ester To a solution of 1-(3-aminopropyl)-5-fluoro-3,4-dihydro-1H-quinoxalin-2-one from Example 15A (115 mg, 0.36 mmol) in THF (4 ml) were added a solution of phosgene in toluene (20%, 0.25 ml, 0.47 mmol) and diisopropylethylamine (85 µl, 0.47 mmol). The mixture was stirred for 2 h. To the mixture were added a solution of (4-aminomethyl-3-methylphenyl)-(2,3,4,5-tetrahydrobenzo[b]azepin-1-yl)methanone from Example F (106 mg, 0.36 mmol) in THF (1 ml) and diisopropylethylamine (85 µl, 0.47 mmol). The mixture was stirred for 2 h and evaporated in vacuo. The residue was purified by flash column chromatography on silica (eluant EtOAc:pet. ether 85:15) to give a white solid; yield 145 mg, 63%.

15C. 4-(3-Aminopropyl)-8-fluoro-3-oxo-3,4-dihydro-2H-quinoxaline-1-carboxylic Acid 2-methyl-4-(2,3,4,5-tetrahydrobenzo[b]azepine-1-carbonyl)-benzylamide (3-{5-Fluoro-4-[2-methyl-4-(2,3,4,5-tetrahydrobenzo[b]azepine-1-carbonyl)-benzylcarbamoyl]-2-oxo-3,4-dihydro-2H-quinoxalin-1-yl}propyl)carbamic acid tert-butyl ester from Example 15B (90 mg, 0.14 mmol) was added to a solution of 4N HCl/dioxan (10 ml) and the mixture was stirred for 0.5 h. The mixture was diluted with toluene, evaporated in vacuo and azeotroped with toluene to give a pale yellow solid; yield 82 mg, 100%.

M.S.: calc m/e—543.64; found [M+H]$^+$—544.2

Example 16

8-Fluoro-4-(2-methoxyethyl)-3-oxo-3,4-dihydro-2H-quinoxaline-1-carboxylic Acid 4-(5H,11H-benzo[e]pyrrolo[1,2-a][1,4]diazepine-10-carbonyl)-2-methylbenzylamide

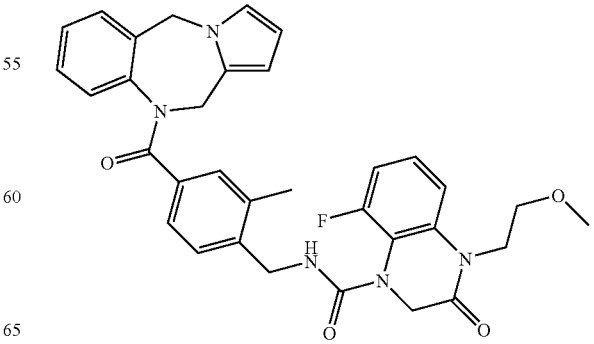

16A. 5-Fluoro-1-(2-methoxyethyl)-3,4-dihydro-1H-quinoxalin-2-one

Sodium hydride (60%, 72 mg, 1.8 mmol) was added to a solution of 5-fluoro-3,4-dihydro-1H-quinoxalin-2-one from Example B (300 mg, 1.8 mmol) in DMF (6.0 ml) while cooling in an ice/water bath. The mixture was allowed to warm to room temperature and stirred for 0.5 h. The mixture was cooled in an ice/water bath and 2-bromoethyl methyl ether (170 µl, 1.8 mmol) and sodium iodide (140 mg, 0.9 mmol) were added. The mixture was allowed to warm to room temperature and stirred for 18 h. The mixture was diluted with brine and evaporated in vacuo. The residue was partitioned between EtOAc and brine and separated. The organic phase was dried and evaporated. The residue was purified by flash chromatography (eluant EtOAc:pet.ether 55:45) to give a pale yellow gum; yield 200 mg, 50%.

16B. 8-Fluoro-4-(2-methoxyethyl)-3-oxo-3,4-dihydro-2H-quinoxaline-1-carboxylic Acid 4-(5H,11H-benzo[e]pyrrolo[1,2-a][1,4]diazepine-10-carbonyl)-2-methylbenzylamide To a solution of 5-fluoro-1-(2-methoxyethyl)-3,4-dihydro-1H-quinoxalin-2-one from Example 16A (100 mg, 0.44 mmol) in toluene (7.0 ml) were added trichloromethyl chloroformate (54 µl, 0.45mmol), diisopropylethylamine (81 µl, 0.45 mmol) and a spatula full of activated carbon. The mixture was heated at reflux for 2 h. The mixture was cooled to room temperature, filtered through Celite® and evaporated. The residue was taken up in THF (5.0 ml) and added to a solution of (4-aminomethyl-3-methylphenyl)-(5H,11H-benzo[e]pyrrolo[1,2-a][1,4]diazepin-10-yl)methanone from Example G (145 mg, 0.44 mmol) in THF (5.0 ml) and diisopropylethylamine (81 µl, 0.45 mmol) while cooling in an ice/water bath. The mixture was allowed to warm to room temperature, stirred for 18 h and evaporated in vacuo. The residue was purified by flash column chromatography on silica (eluant EtOAc:pet. ether 90:10) to give an off-white solid; yield 200 mg, 78%.

M.S.: calc m/e—581.64; found [M+H]⁺—582.2

Example 17

{4-[4-(5H,11H-Benzo[e]pyrrolo[1,2-a][1,4]diazepine-10-carbonyl)-2-methylbenzylcarbamoyl]-5-fluoro-2-oxo-3,4-dihydro-2H-quinoxalin-1-yl}acetic Acid Methyl Ester

17A. (5-Fluoro-2-oxo-3,4-dihydro-2H-quinoxalin-1-yl)acetic Acid Methyl Ester To a solution of 5-fluoro-3,4-dihydro-1H-quinoxalin-2-one from Example B (150 mg, 0.90 mmol) in DMF (3.0 ml) was added sodium hydride (60%, 36 mg, 0.90 mmol) while cooling in an ice/water bath. The mixture was allowed to warm to room temperature and stirred for 0.5 h. The mixture was cooled again in an ice/water bath and methyl bromoacetate (85 µl, 0.90 mmol) was added. The mixture was allowed to warm slowly to room temperature and stirred for 18 h. Brine was added and the mixture was evaporated in vacuo. The residue was partitioned between EtOAc and brine and separated. The organic phase was dried and evaporated in vacuo. The residue was purified by flash chromatography on silica (eluant EtOAc:pet ether 40:60) to give a white solid; yield 140 mg, 65%.

17B. {4-[4-(5H,11H-Benzo[e]pyrrolo[1,2-a][1,4]diazepine-10-carbonyl)-2-methylbenzylcarbamoyl]-5-fluoro-2-oxo-3,4-dihydro-2H-quinoxalin-1-yl}acetic Acid Methyl Ester To a solution of (5-fluoro-2-oxo-3,4-dihydro-2H-quinoxalin-1-yl)acetic acid methyl ester from Example 17A (72 mg, 0.30 mmol) in toluene (5.0 ml) were added trichloromethyl chloroformate (36 µl, 0.30 mmol), diisopropylethylamine (54 µl, 0.30 mmol) and a spatula full of activated carbon. The mixture was heated at reflux for 2 h. The mixture was cooled to room temperature, filtered through Celite® and evaporated. The residue was taken up in THF (4.0 ml) and added to a solution of (4-aminomethyl-3-methylphenyl)-(5H,11H-benzo[e]pyrrolo[1,2-a][1,4]diazepin-10-yl)methanone from Example G (9 9mg, 0.30 mmol) in THF (4.0 ml) and diisopropylethylamine (54 µl, 0.30 mmol) while cooling in an ice/water bath. The mixture was allowed to warm to room temperature, stirred for 18 h and evaporated in vacuo. The residue was purified by flash column chromatography on silica (eluant EtOAc:pet. ether 75:25) to give a white solid; yield 61 mg, 34%.

M.S.: calc m/e—595.63; found [M+H]⁺—596.2

Example 18

8-Fluoro-4-methyl-3-oxo-3,4-dihydro-2H-quinoxaline-1-carboxylic Acid 4-(5H,11H-benzo[e]pyrrolo[1,2-a][1,4]dizaepine-10-carbonyl)-2-methylbenzylamide

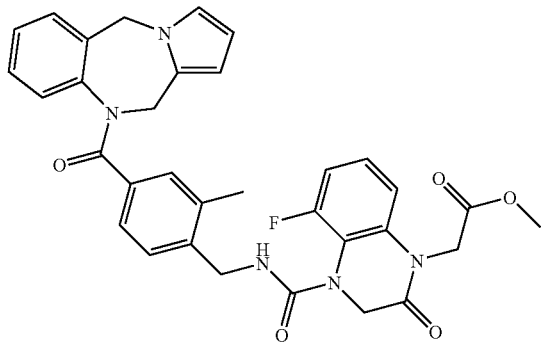

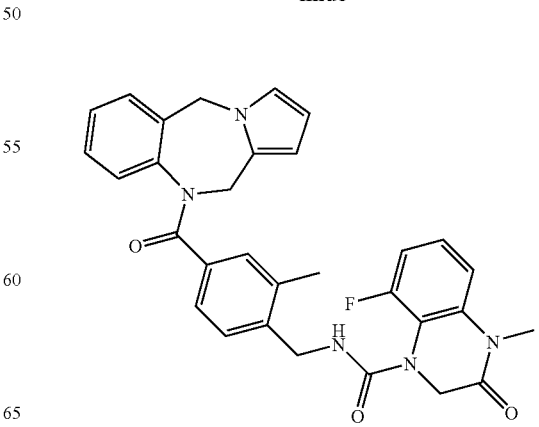

18A.
5-Fluoro-1-methyl-3,4-dihydro-1H-quinoxalin-2-one

To a solution of 5-fluoro-3,4-dihydro-1H-quinoxalin-2-one from Example B (415 mg, 2.5 mmol) in THF (10 ml) was added sodium hydride (60%, 100 mg, 2.5 mmol) while cooling in an ice/water bath. The mixture was allowed to warm to room temperature and stirred for 0.5 h. The mixture was cooled again in an ice/water bath and iodomethane (156 µl, 2.5 mmol) was added. The mixture was allowed to warm slowly to room temperature and stirred for 3 days. Brine was added and the mixture was evaporated in vacuo. The residue was partitioned between EtOAc and brine and separated. The organic phase was washed with brine, dried and evaporated in vacuo. The residue was purified by flash chromatography on silica (eluant EtOAc:pet ether 45:55) to give a white solid; yield 210 mg, 47%.

18B. 8-Fluoro-4-methyl-3-oxo-3,4-dihydro-2H-quinoxaline-1-carboxylic Acid 4-(5H,11H-benzo[e]pyrrolo[1,2-a][1,4]diazepine-10-carbonyl)-2-methyl-benzylamide To a solution of 5-fluoro-1-methyl-3,4-dihydro-1H-quinoxalin-2-one from Example 18A (72 mg, 0.40 mmol) in toluene (4.0 ml) were added trichloromethyl chloroformate (48 µl, 0.40 mmol), diisopropylethylamine (72 µl, 0.40 mmol) and a spatula full of activated carbon. The mixture was heated at reflux for 2 h. The mixture was cooled to room temperature, filtered through Celite® and evaporated. The residue was taken up in THF (3.0 ml) and added to a solution of (4-aminomethyl-3-methyl-phenyl)-(5H,11H-benzo[e]pyrrolo[1,2-a][1,4]diazepin-10-yl)methanone from Example G (119 mg, 0.36 mmol) in THF (5.0 ml) and diisopropylethylamine (72 µl, 0.40 mmol) while cooling in an ice/water bath. The mixture was allowed to warm to room temperature, stirred for 1.5 h and evaporated in vacuo. The residue was purified by flash column chromatography on silica (eluant EtOAc:pet. ether 85:15) to give a pale yellow solid; yield 112 mg, 58%.

M.S.: calc m/e—537.60; found [M+H]⁺—538.2

Example 19

9-Fluoro-5-oxo-2,3-dihydro-5H-benzo[e][1,4]oxazepine-1-carboxylic Acid 2-methyl-4-(2,3,4,5-tetrahydrobenzo[b]azepine-1-carbonyl)benzylamide

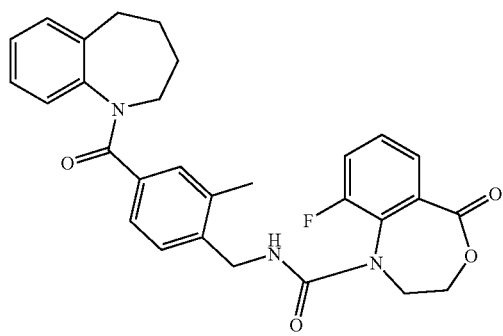

19A. 2-tert-Butoxycarbonylamino-3-fluorobenzoic Acid

A solution of tert-butyllithium in pentane (1.7M, 34 ml, 58 mmol) was added with caution to a solution of (2-fluoro-phenyl)-carbamic acid tert-butyl ester whilst cooling to less than −50° C. The mixture was maintained at this temperature, stirred for 3 h then poured onto a slurry of THF and dry ice. The mixture was allowed to warm to room temperature, diluted with water and evaporated in vacuo. The residue was taken up in water and washed with diethyl ether. A solution of 0.3M potassium hydrogen sulphate was added until pH6 and extracted with chloroform. The chloroform extracts were combined, washed with brine, dried and reduced to give a white solid; yield 2.7 g, 37%.

19B. 2-tert-Butoxycarbonylamino-3-fluorobenzoic Acid 2-(tert-butyldimethylsilanyloxy)ethyl Ester To a solution of caesium carbonate (1.63 g, 5.0 mmol) in DMF (10 ml) was added 2-tert-butoxycarbonylamino-3-fluoro-benzoic acid from Example 19A (1.15 g, 4.5 mmol), (2-bromoethoxy)-tert-butyldimethylsilane (1.08 g, 4.5 ml) and sodium iodide (680 mg, 4.5 ml). The mixture was heated at 65° C. for 3 h and evaporated in vacuo. The residue was partitioned between chloroform and brine and the organic phase was dried and evaporated in vacuo. The residue was purified by flash chromatography on silica (eluant EtOAc: pet. ether 15:85) to give a colourless gum; yield 1.1 g, 59%.

19C. 2-tert-Butoxycarbonylamino-3-fluorobenzoic Acid 2-hydroxyethyl Ester

To a solution of 2-tert-butoxycarbonylamino-3-fluorobenzoic acid 2-(tert-butyldimethylsilanyloxy)ethyl ester from Example 19B (1.2 g, 2.9 mmol) in THF (25 ml) was added a solution tetrabutylammonium fluoride (1.0M, 5.8 ml, 5.8 mmol) in THF while cooling in an ice/water bath. The mixture was allowed to warm to room temperature and stirred for 18 h. Saturated ammonium chloride solution (20 ml) was added and the mixture was stirred for 1 h and evaporated in vacuo. The residue was partitioned between chloroform and water and the organic phase was dried and evaporated in vacuo. The residue was purified by flash chromatography on silica (eluant EtOAc:pet.ether 90:10) to give a colourless gum; yield 180 mg, 21%.

19D. 9-Fluoro-5-oxo-2,3-dihydro-5H-benzo[e][1,4]oxazepine-1-carboxylic Acid Tert-Butyl Ester Triphenyl phosphine (204 mg, 0.78 mmol) and diethylazodicarboxylate from Example 19C (136 mg, 0.78 mmol) were added to a solution of 2-tert-butoxycarbonylamino-3-fluoro-benzoic acid 2-hydroxy-ethyl ester (180 mg, 0.60 mmol) in THF (6.0 ml) while cooling in an ice/water bath. The mixture was allowed to warm to room temperature, stirred for 3 days and evaporated in vacuo. The residue was purified by flash chromatography on silica (eluant EtOAc:pet ether 70:30 then again with EtOAc:pet ether 40:60) to give a white solid; yield 50 mg, 30%.

19E. 9-Fluoro-2,3-dihydro-1H-benzo[e][1,4]oxazepin-5-one; Hydrochloride

9-Fluoro-5-oxo-2,3-dihydro-5H-benzo[e][1,4]oxazepine-1-carboxylic acid tert-butyl ester from Example 19D (50 mg, 0.18 mmol) was added to a solution of hydrogen chloride in dioxan (4N, 3 ml) and stirred for 1 h. The mixture was diluted with toluene, evaporated in vacuo and azeotroped with toluene to give a white solid; yield 35 mg, 90%.

19F. 9-Fluoro-5-oxo-2,3-dihydro-5H-benzo[e][1,4]oxazepine-1-carboxylic Acid 2-methyl-4-(2,3,4,5-tetrahydrobenzo[b]azepin-1-carbonyl)benzylamide To a solution of 9-fluoro-2,3-dihydro-1H-benzo[e][1,4]oxazepin-5-one; hydrochloride from Example 19E (22 mg, 0.12 mmol) in toluene (3.0 ml) were added trichloromethyl chloroformate (15 µl. 0.12 mmol), diisopropylethylamine (22 µl, 0.12 mmol) and a spatula full of activated carbon. The mixture was heated at reflux for 2 h. The mixture was cooled to room temperature, filtered through Celite® and evaporated. The residue was taken up in THF (2.0 ml) and added to a solution of (4-aminomethyl-3-methylphenyl)-(2,3,4,5-tetrahydrobenzo[b]azepin-1-yl)methanone from Example F (35 mg, 0.12 mmol) in THF (2.0 ml) and diisopropylethylamine (22 µl, 0.12 mmol) while cooling in an ice/water bath. The mixture was allowed to warm to room temperature, stirred for 2 h and evaporated in vacuo. The residue was purified by flash column chromatography on silica (eluant EtOAc:pet. ether 80:20) to give a white solid; yield 12 mg, 20%.

M.S.: calc m/e—501.6; found [M+H]$^+$—502.3

Example 20

9-Fluoro-5-oxo-2,3,4,5-tetrahydrobenzo[e][1,4]diazepine-1-carboxylic Acid 2-methyl-4-(2,3,4,5-tetrahydrobenzo[b]azepin-1-carbonyl)benzylamide

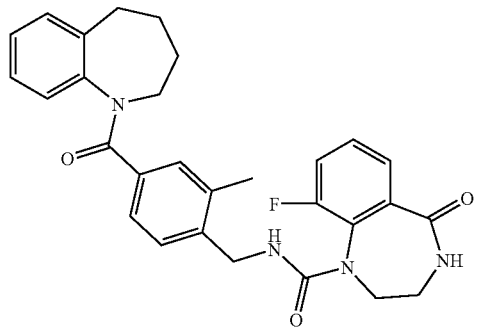

20A. 2-tert-Butoxycarbonylamino-3-fluorobenzoic Acid Methyl Ester

To a suspension of caesium carbonate (1.3 g, 4.0 mmol) in DMF (5.0 ml) was added 2-tert-butoxycarbonylamino-3-fluorobenzoic acid from Example 19A (890 mg, 3.5 mmol) and iodomethane (230 µl, 3.8 mmol). The mixture was stirred for 18 h and evaporated in vacuo. The residue was partitioned between EtOAc and brine and the organic layer was dried and evaporated in vacuo. The residue was purified by flash chromatography on silica (eluant EtOAc;pet. ether 25:75) to give a white solid; yield 680 mg, 72%.

20B. 2-[(2-Benzyloxycarbonylaminoethyl)-tert-butoxycarbonylamino]-3-fluorobenzoic Acid Sodium hydride (60%, 120 mg, 3.0 mmol) was added to a solution of 2-tert-butoxycarbonylamino-3-fluorobenzoic acid methyl ester from Example 20A (750 mg, 2.8 mmol) in DMF (8.0 ml) while cooling in an ice/water bath. The mixture was allowed to warm to room temperature and stirred for 30 min. (2-bromoethyl)carbamic acid benzyl ester (360 mg, 2.8 mmol) and sodium iodide (420 mg, 2.8 mmol) were added and the mixture was heated at 65° C. for 18 h. The mixture was cooled and evaporated in vacuo. The residue was partitioned between EtOAc and brine and the organic layer was dried and evaporated in vacuo. The residue was purified by flash chromatography on silica (EtOAc:pet. ether 30:70) to give a colourless gum; yield 340 mg, 27%.

20C. 9-Fluoro-5-oxo-2,3,4,5-tetrahydrobenzo[e][1,4]diazepine-1-carboxylic Acid Tert-Butyl Ester A solution of 2-[(2-benzyloxycarbonylaminoethyl)-tert-butoxycarbonylamino]-3-fluorobenzoic acid from Example 20B (390 mg, 0.87 mmol), 10% palladium/carbon (~100 mg) and acetic acid (1.0 ml) in methanol (25 ml) was hydrogenated at atmospheric pressure for 1.5 h. The mixture was filtered, evaporated in vacuo and azeotroped with toluene. The residue was taken up in a mixture of IPA and acetic acid (90:10, 35 ml) and heated at reflux for 4 h. The mixture was cooled, evaporated in vacuo and azeotroped with toluene to give a white solid; yield 250 mg, 100%.

20D. 9-Fluoro-1,2,3,4-tetrahydrobenzo[e][1,4]diazepin-5-one; Hydrochloride

9-Fluoro-5-oxo-2,3,4,5-tetrahydrobenzo[e][1,4]diazepine-1-carboxylic acid tert-butyl ester from Example 20C (245 mg, 0.88 mmol) was added to a solution of hydrogen chloride in dioxan (4N, 10 ml) and stirred for 1 h. The mixture was diluted with toluene, evaporated in vacuo and azeotroped with toluene to give a white solid; yield 170 mg, 90%.

20E. 9-Fluoro-5-oxo-2,3,4,5-tetrahydrobenzo[e][1,4]diazepine-1-carboxylic Acid 2-methyl-4-(2,3,4,5-tetrahydrobenzo[b]azepine-1-carbonyl)benzylamide To a solution of 9-fluoro-1,2,3,4-tetrahydrobenzo[e][1,4]diazepin-5-one; hydrochloride from Example 20D (20 mg, 0.11 mmol) in toluene (3.0 ml) were added trichloromethyl chloroformate (14 µl, 0.11 mmol), diisopropylethylamine (20 µl, 0.11 mmol) and a spatula full of activated carbon. The mixture was heated at reflux for 2 h. The mixture was cooled to room temperature, filtered through Celite® and evaporated. The residue was taken up in THF (2.0 ml) and added to a solution of (4-aminomethyl-3-methylphenyl)-(2,3,4,5-tetrahydrobenzo[b]azepin-1-yl)methanone from Example F (32 mg, 0.11 mmol) in THF (2.0 ml) and diisopropylethylamine (20 µl, 0.11 mmol) while cooling in an ice/water bath. The mixture was allowed to warm to room temperature, stirred for 2 h and evaporated in vacuo. The residue was purified by flash chromatography on silica (eluant methanol:CH$_2$Cl$_2$ 4:96) to give a white solid; yield 6 mg, 11%.

M.S.: calc m/e—500.6; found [M+H]$^+$—501.4

Example 21

8-Fluoro-4-(2-hydroxyethyl)-3-oxo-3,4-dihydro-2H-quinoxaline-1-carboxylic Acid 4-[(2-furan-2-ylphenyl)methylcarbamoyl]-2-methylbenzylamide

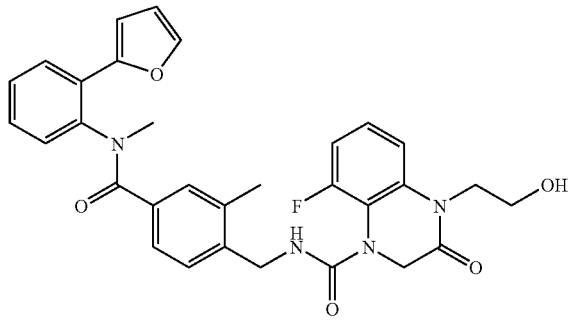

21A. 2-Furan-2-ylphenylamine

To a solution of 2-bromoaniline (137 mg, 0.80 mmol) in THF (4.0 ml) was added 2-furanboronic acid (89 mg, 0.80 mmol), tetrakis-(triphenylphosphine)palladium (0) (92 mg, 0.08 mmol) and sodium carbonate solution (2M, 2.0 ml, 4.0 mmol). The mixture was heated in a sealed tube using a microwave reactor (20 W) at 130° C. for 25 min. This procedure was carried out 5 times and the reaction mixtures were combined. The mixture was separated and the aqueous layer extracted with EtOAc. The combined organic layers were dried and evaporated in vacuo. The residue was purified by flash chromatography on silica (eluant pet. ether:EtOAc 85:15) to give a brown oil; yield 211 mg, 33%.

21B. 4-Cyano-N-(2-furan-2-ylphenyl)-3-methylbenzamide

To a solution of 4-cyano-3-methylbenzoic acid from Example C (187 mg, 1.16 mmol) in toluene (10 ml) was added thionyl chloride (425 µl, 5.8 mmol). The mixture was heated at reflux for 2 h, cooled, evaporated in vacuo and azeotroped with toluene. The residue was taken up in CH$_2$Cl$_2$ (5.0 ml) and added to a solution of 2-furan-2-yl-phenylamine from Example 21A (185 mg, 1.16 mmol) and triethylamine (324 µl, 2.32 mmol) in CH$_2$Cl$_2$ (5.0 ml). The mixture was stirred for 18 h, partitioned between water and chloroform and separated. The organic layers were dried and evaporated in vacuo. The residue was purified by flash chromatography on silica (eluant pet. ether:EtOAc 80:20) to give a yellow solid; yellow solid 233 mg, 66%.

21C. 4-Cyano-N-(2-furan-2-ylphenyl)-3,N-dimethylbenzamide

To a solution of 4-cyano-N-(2-furan-2-ylphenyl)-3-methylbenzamide from Example 21B (222 mg, 0.734 mmol) in DMF (8.0 ml) was added sodium hydride (60%, 44 mg, 1.10 mmol) while cooling in an ice/water bath. The mixture was allowed to warm to room temperature and stirred for 45 min. Iodomethane (68 µl, 1.10 mmol) was added and the mixture was stirred for 18 h. The mixture was evaporated in vacuo and the residue was taken up in EtOAc, washed with brine, dried and evaporated in vacuo. The residue was purified by flash chromatography on silica (eluant pet.ether:EtOAc 80:20) to give a brown solid; yield 198 mg, 85%.

21D. 4-Aminomethyl-N-(2-furan-2-ylphenyl)-3,N-dimethylbenzamide

To a solution of 4-cyano-N-(2-furan-2-ylphenyl)-3,N-dimethylbenzamide from Example 21C (198 mg, 0.626 mmol) in methanol (10 ml) was added cobalt (II) hexahydrate (300 mg, 1.25 mmol). The mixture was cooled in an ice/water bath and sodium borohydride (237 mg, 6.26 mmol) was added portionwise. The mixture was allowed to warm to room temperature and stirred for 2 h. Ammonia solution (4.0 ml) was added and the mixture stirred for 30 min, filtered through Celite® and evaporated in vacuo. The residue was taken up in chloroform and brine, filtered through Celite®, separated and the organic layer was dried and evaporated in vacuo to give a white solid; yield 200 mg, 100%.

21E. 1-[2-(tert-Butyldimethylsilanyloxy)ethyl]-5-fluoro-3,4-dihydro-1H-quinoxalin-2-one Sodium hydride (60%, 128 mg, 3.2 mmol) was added to a solution of 5-fluoro-3,4-dihydro-1H-quinoxalin-2-one from Example B (530 mg, 3.2 mmol) while cooling in an ice/water bath. The mixture was allowed to warm to room temperature and stirred for 10 min. (2-Bromoethoxy)-tert-butyldimethylsilane (789 mg, 3.3 mmol) and sodium iodide (495 mg, 3.3 mmol) were added and the mixture was stirred for 18 h. Brine was added and the mixture was evaporated in vacuo. The residue was taken up in EtOAc and brine, separated and the organic layer was dried and evaporated in vacuo. The residue was purified by flash chromatography on silica (eluant EtOAc:pet.ether 40:60) to give a pale yellow solid: yield 600 mg, 58%.

21F. 4-[2-(tert-Butyldimethylsilanyloxy)ethyl]-8-fluoro-3-oxo-3,4-dihydro-2H-quinoxaline-1-carboxylic Acid 4-[(2-furan-2-ylphenyl)methylcarbamoyl]-2-methylbenzylamide A solution of 1-[2-(tert-butyldimethylsilanyloxy)ethyl]-5-fluoro-3,4-dihydro-1H-quinoxalin-2-one from Example 21E (110 mg, 0.34 mmol) and diisopropylethylamine (77 µl, 0.44 mmol) in THF (8.0 ml) and a solution of phosgene in toluene (20%, 233 µl, 0.44 mmol) were stirred together for 2 h. A solution of 4-aminomethyl-N-(2-furan-2-ylphenyl)-3,N-dimethylbenzamide from Example 21D (108 mg, 0.34 mmol) and diisopropylethylamine (77 µl, 0.44 mmol) in THF (5.0 ml) was added and the mixture was stirred for 18 h and evaporated in vacuo. The residue was directly in the next step of the synthesis as described in Example 21G.

21G. 8-Fluoro-4-(2-hydroxyethyl)-3-oxo-3,4-dihydro-2H-quinoxaline-1-carboxylic Acid 4-[(2-furan-2-ylphenyl)methylcarbamoyl]-2-methylbenzylamide To a solution of 4-[2-(tert-butyldimethylsilanyloxy)ethyl]-8-fluoro-3-oxo-3,4-dihydro-2H-quinoxaline-1-carboxylic acid 4-[(2-furan-2-ylphenyl)methylcarbamoyl]-2-methylbenzylamide from Example 21F (0.34 mmol) in THF (5.0 ml) was added a solution of tetrabutylammonium fluoride in THF (1.0 M, 1.0 ml, 1.0 mmol) while cooling in an ice/water bath. The mixture was allowed to warm to room temperature and stirred for 3 days. The mixture was evaporated in vacuo and the residue was taken up in CH$_2$Cl$_2$ and washed with ammonium chloride solution. The organic phase was dried and evaporated in vacuo and the residue was purified by flash chromatography on silica (eluant CHCl₃:methanol 95:5) to give a white solid; yield 120 mg, 64%.

Following the above methods, the following compounds were also prepared.

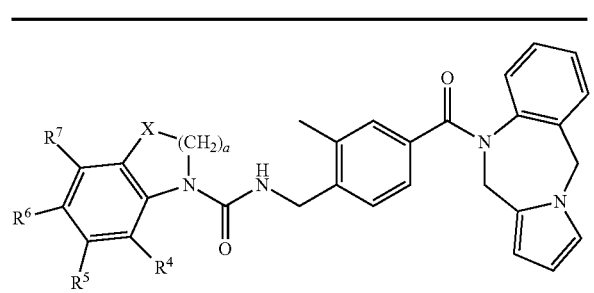

| Ex. | X | R⁴ | R⁵ | R⁶ | R⁷ | a | MS (MH⁺) |
|---|---|---|---|---|---|---|---|
| 22 | CH₂ | H | H | H | H | 1 | 477.1 |
| 23 | CH₂ | F | H | H | H | 1 | 495.2 |
| 24 | CH₂ | H | H | H | H | 2 | 491.2 |
| 25 | CH₂ | CH₃ | H | H | H | 2 | 505.2 |
| 26 | CH₂ | H | CH₃ | H | H | 2 | 505.2 |
| 27 | CH₂ | H | H | CH₃ | H | 2 | 505.2 |
| 28 | CH₂ | OCH₃ | H | H | H | 2 | 521.1 |
| 29 | CH₂ | Cl | H | H | H | 2 | 525.2 |
| 30 | CH₂ | H | H | Cl | H | 2 | 525.1 |
| 31 | CH₂ | H | H | H | Cl | 2 | 525.2 |
| 32 | O | H | H | H | H | 2 | 492.6 |
| 33 | O | F | H | H | H | 2 | 511.2 |
| 34 | O | H | Cl | H | H | 2 | 527.1 |
| 35 | O | H | CH₃ | H | H | 2 | 507.2 |
| 36 | S | H | H | H | H | 2 | 509.1 |
| 37 | C=O | H | H | H | H | 3 | 643.3 |
| 38 | C=O | F | H | H | H | 2 | 522.9 |
| 39 | NCH₃ | Cl | H | H | H | 2 | 540.2 |
| 40 | NCH₃ | F | H | H | H | 2 | 524.2 |
| 41 | NCH₃ | F | F | H | H | 2 | 542.2 |
| 42 | NCH₂CH₃ | F | H | H | H | 2 | 538.0 |
| 43 | CH₂ | F | H | H | H | 2 | 509.2 |
| 44 | CH₂ | F | H | F | H | 2 | 527.2 |
| 45 | CH₂ | F | F | F | H | 2 | 545.2 |
| 46 | CH₂ | F | F | F | F | 2 | 563.2 |
| 47 | NH | F | H | H | H | 2 | 510.2 |
| 48 | NC(=O)CH₂OCH₃ | F | H | H | H | 2 | 582.2 |
| 49 | NC(=O)CH₂CH₂OCH₃ | F | H | H | H | 2 | 596.2 |
| 50 | NCH₂CH₂OH | F | H | H | H | 2 | 554.2 |
| 51 | NCH₂COOC(CH₃)₃ | F | H | H | H | 2 | 624.1 |
| 52 | N-CH₂-phenyl | F | H | H | H | 2 | 600.3 |

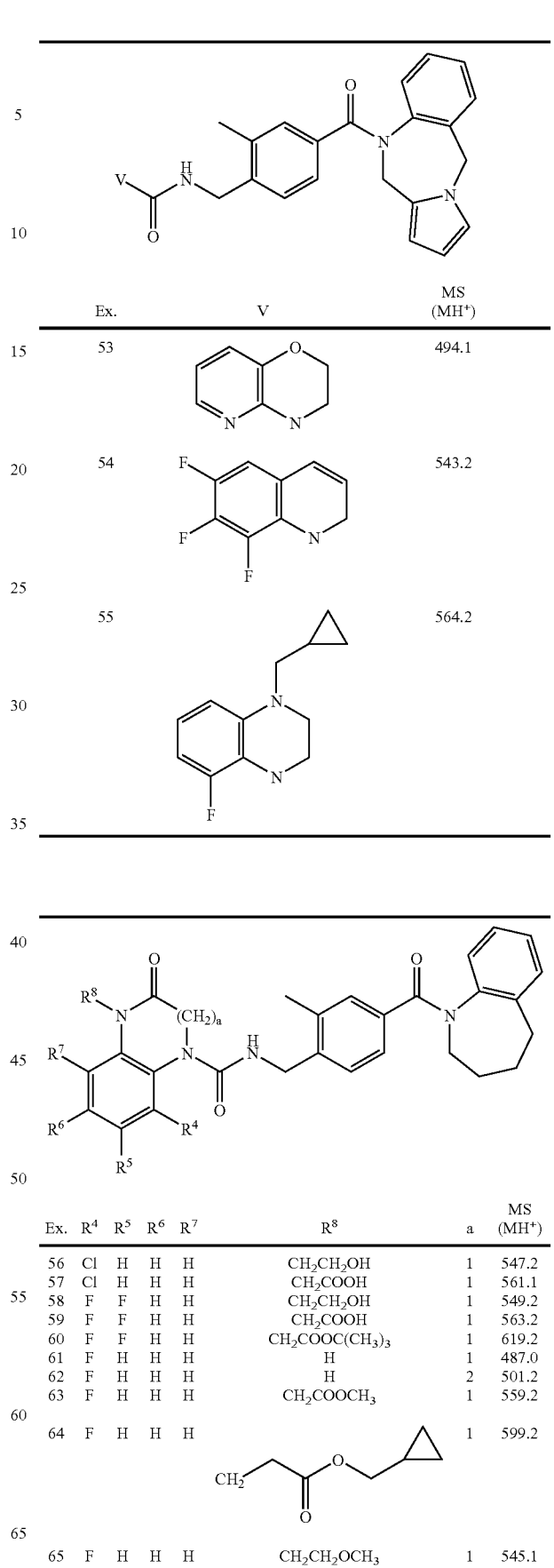

| Ex. | V | MS (MH⁺) |
|---|---|---|
| 53 | pyrido-oxazine | 494.1 |
| 54 | trifluoroquinoline | 543.2 |
| 55 | cyclopropylmethyl-fluoro-tetrahydroquinoxaline | 564.2 |

| Ex. | R⁴ | R⁵ | R⁶ | R⁷ | R⁸ | a | MS (MH⁺) |
|---|---|---|---|---|---|---|---|
| 56 | Cl | H | H | H | CH₂CH₂OH | 1 | 547.2 |
| 57 | Cl | H | H | H | CH₂COOH | 1 | 561.1 |
| 58 | F | F | H | H | CH₂CH₂OH | 1 | 549.2 |
| 59 | F | F | H | H | CH₂COOH | 1 | 563.2 |
| 60 | F | F | H | H | CH₂COOC(CH₃)₃ | 1 | 619.2 |
| 61 | F | H | H | H | H | 1 | 487.0 |
| 62 | F | H | H | H | H | 2 | 501.2 |
| 63 | F | H | H | H | CH₂COOCH₃ | 1 | 559.2 |
| 64 | F | H | H | H | CH₂C(=O)O-CH₂-cyclopropyl | 1 | 599.2 |
| 65 | F | H | H | H | CH₂CH₂OCH₃ | 1 | 545.1 |

-continued

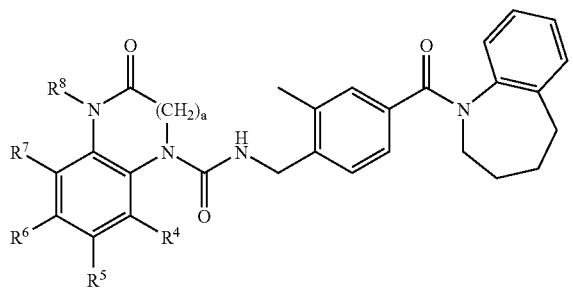

| Ex. | R⁴ | R⁵ | R⁶ | R⁷ | R⁸ | a | MS (MH⁺) |
|---|---|---|---|---|---|---|---|
| 66 | F | H | H | H | CH$_2$CH$_2$OCH$_2$CH$_3$ | 1 | 559.1 |
| 67 | F | H | H | H | CH$_2$CH$_2$OCOCH$_3$ | 1 | 573.0 |
| 68 | F | H | H | H | CH$_2$CH$_2$NH$_2$ | 1 | 530.2 |
| 69 | F | H | H | H | CH$_2$CH$_2$N(CH$_3$)$_2$ | 1 | 586.3 |
| 70 | F | H | H | H | CH$_2$CH$_2$CH$_2$OCOCH$_3$ | 1 | 587.1 |
| 71 | F | H | H | H | CH$_2$CH(CH$_3$)$_2$ | 1 | 542.7 |
| 72 | F | H | H | H | CH$_2$CONH$_2$ | 1 | 544.4 |

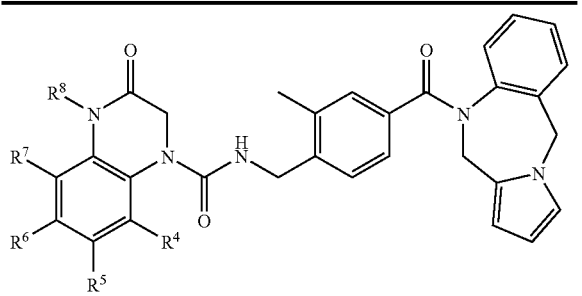

| Ex. | R⁴ | R⁵ | R⁶ | R⁷ | R⁸ | MS (MH⁺) |
|---|---|---|---|---|---|---|
| 73 | Cl | H | H | H | H | 540.2 |
| 74 | F | F | H | H | CH$_2$CH$_2$OH | 586.1 |
| 75 | F | F | H | H | CH$_2$COOH | 600.2 |
| 76 | F | F | H | H | CH$_2$COOC(CH$_3$)$_3$ | 656.1 |
| 77 | F | H | H | H | CH$_2$CH$_2$CH$_2$OH | 582.1 |
| 78 | F | H | H | H | CH$_2$CH$_2$COOH | 596.2 |
| 79 | F | H | H | H | CH$_2$CH$_2$COOCH$_2$CH$_3$ | 624.2 |
| 80 | F | F | H | H | CH$_3$ | 556.1 |
| 81 | F | H | H | H | H | 524.2 |
| 82 | F | F | H | H | H | 542.1 |
| 83 | F | F | F | H | H | 560.2 |
| 84 | F | H | H | H | CH$_2$CON(CH$_3$)$_2$ | 609.2 |
| 85 | F | H | H | H | CH$_2$CH$_2$CH$_2$OCOCH$_3$ | 624.2 |
| 86 | F | H | H | H | CH$_2$CH$_2$OCH$_2$CH$_3$ | 596.1 |
| 87 | F | H | H | H | CH$_2$OCH$_3$ | 568.0 |
| 88 | F | H | H | H | CH$_2$CH$_2$OH | 568.1 |
| 89 | F | H | H | H | CH$_2$COOH | 582.2 |
| 90 | F | H | H | H | CH$_2$COOC(CH$_3$)$_3$ | 638.1 |
| 91 | F | H | H | H | 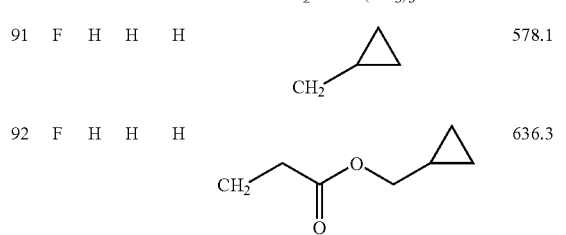 | 578.1 |
| 92 | F | H | H | H | 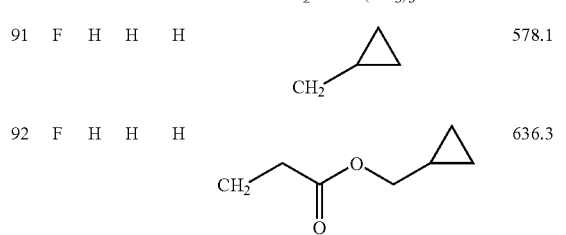 | 636.3 |

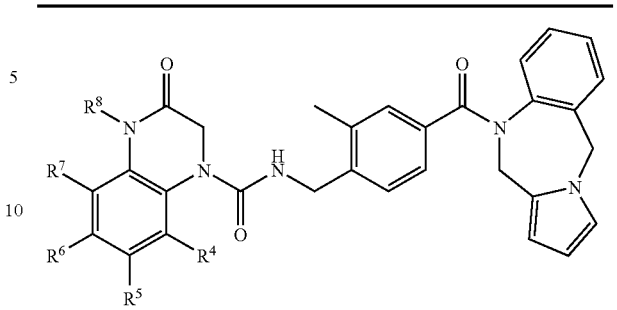

| Ex. | R⁴ | R⁵ | R⁶ | R⁷ | R⁸ | MS (MH⁺) |
|---|---|---|---|---|---|---|
| 93 | F | H | H | H | (tetrazole-CH$_2$) | 606.4 |
| 94 | F | H | H | H | CH$_2$CH$_3$ | 552.2 |
| 95 | F | H | H | H | CH$_2$CH$_2$NH$_2$ | 567.4 |
| 96 | F | H | H | H | CH$_2$CN | 563.2 |

| Ex. | R⁸ | G¹ | MS (MH⁺) |
|---|---|---|---|
| 97 | H$_3$C | 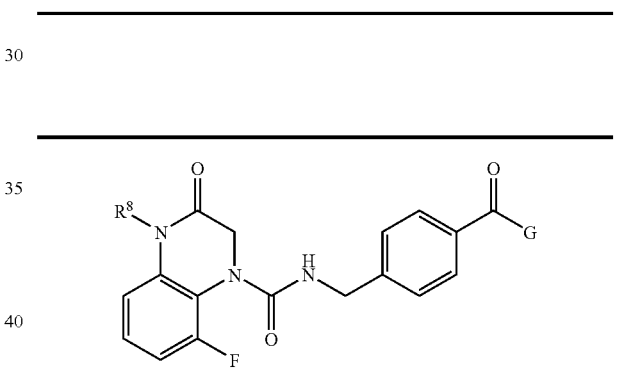 | 524.2 |
| 98 | H | 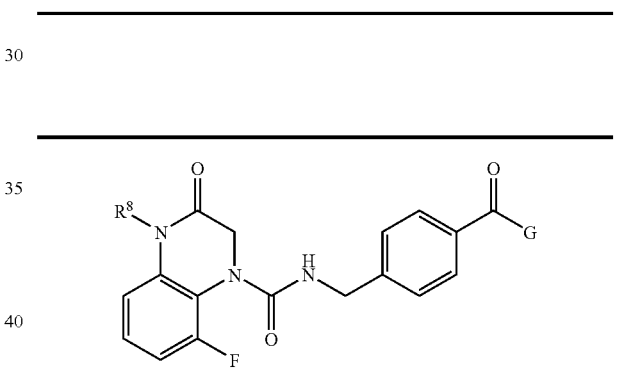 | 475.3 |

| Ex. | R⁸ | G¹ | MS (MH⁺) |
|---|---|---|---|
| 99 | H₃C | 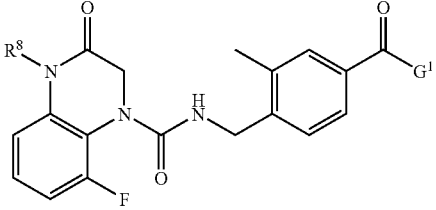 | 552.2 |
| 100 | H₃C | 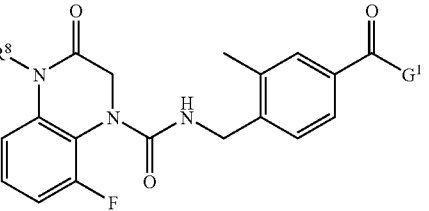 | 539.2 |
| 101 | H₃C | 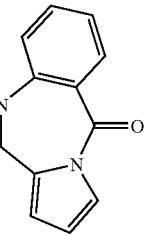 | 557.1 |
| 102 | H₃C | 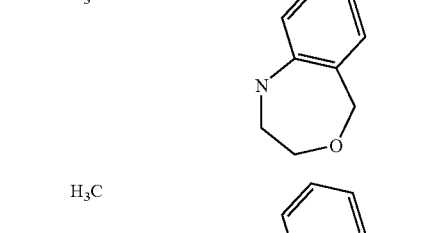 | 502.1 |
| 103 | H₃C | 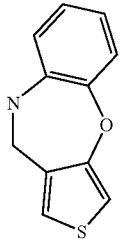 | 530.2 |
| 104 | H | 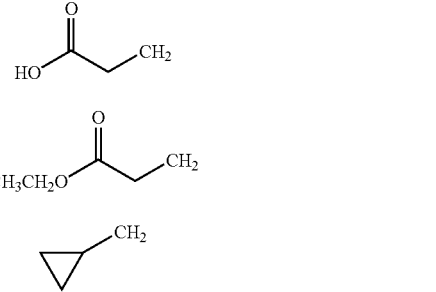 | 532.4 |
| 105 | H₃C | 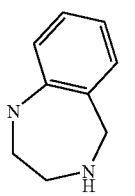 | 503.1 |
| 106 | H₃C | 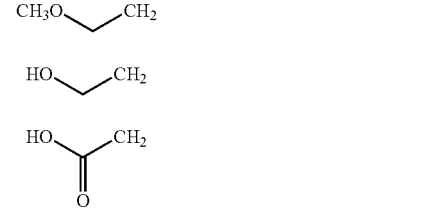 | 503.2 |
| 107 | | HO-CH₂ | 547.2 |
| 108 | | HOOC-CH₂ | 561.1 |
| 109 | | CH₃CH₂OOC-CH₂ | 589.2 |
| 110 | |  | 543.1 |
| 111 | | CH₃O-CH₂ | 547.1 |
| 112 | | HO-CH₂ | 533.2 |
| 113 | | HOOC-CH₂ | 547.2 |
| 114 | | CH₃OOC-CH₂ | 561.3 |
| 115 | | (CH₃)₃C-O-CO-CH₂ | |
| 116 | | H₂N-CH₂ | 532.0 |

-continued

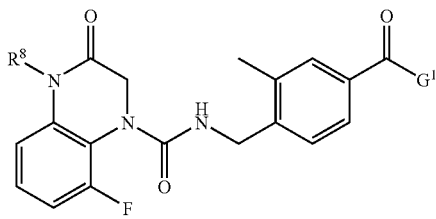

| Ex. | R⁸ | G¹ | MS (MH⁺) |
|---|---|---|---|
| 117 | tetrazol-5-yl-CH₂ | | 571.2 |
| 118 | NC-CH₂ | | 528.1 |
| 119 | CH₃NH-C(O)-CH₂ | | 560.2 |
| 120 | (CH₃)₂N-C(O)-CH₂ | | 574.2 |
| 121 | H | 5,5-difluoro-2,3,4,5-tetrahydro-1H-benzo[b]azepin-1-yl | 523.3 |
| 122 | tBuO-C(O)-CH₂ | | 637.3 |
| 123 | HO-C(O)-CH₂ | | 581.3 |
| 124 | HO-CH₂ | | 567.4 |
| 125 | H | 5-hydroxy-2,3,4,5-tetrahydro-1H-benzo[b]azepin-1-yl | 503.4 |
| 126 | H | 2,3,4,5-tetrahydro-1,5-benzothiazepin-1-yl | 505.3 |

-continued

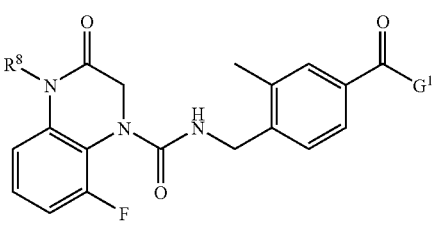

| Ex. | R⁸ | G¹ | MS (MH⁺) |
|---|---|---|---|
| 127 | H | 4,5-dihydro-3H-benzo[b]thiepine 1,1-dioxide-N-yl | 537.3 |
| 128 | H | 2-methyl-4,5-dihydro-2H-pyrazolo-benzazepinyl | 539.4 |
| 129 | H | 5-oxo-2,3,4,5-tetrahydro-1H-benzo[b]azepin-1-yl | 501.4 |
| 130 | H | 5,6,7,8-tetrahydrothieno[3,2-b]azepin-4-yl | 493.3 |
| 131 | H | pyrido-benzoxazepinyl | 538.4 |
| 132 | H | 5,6-dihydrodibenzo[b,d]azepinyl | 535.6 |

-continued

| Ex. | R⁸ | G¹ | MS (MH⁺) |
|---|---|---|---|
| 133 | H | (4,5-dihydrothieno-benzazepine) | 541.1 |

| Ex. | G² | G¹ | MS (MH⁺) |
|---|---|---|---|
| 134 | (3,4-dihydroquinoline) | (methylpyrazolo-benzodiazepine-NH) | |
| 135 | (3,4-dihydroquinoline) | (pyrido-benzoxazepine) | |
| 136 | (dihydrobenzothiazine) | | |

-continued

| Ex. | G² | G¹ | MS (MH⁺) |
|---|---|---|---|
| 137 | (3,4-dihydroquinoline) | (thieno-benzoxazepine) | 510.2 |

| Ex. | R⁸ | R¹ | R² | R³ | G¹ | MS (MH⁺) |
|---|---|---|---|---|---|---|
| 138 | H | H | Cl | H | (thieno-benzoxazepine) | 563.2 |
| 139 | H | H | Cl | H | (N-methyl-benzodiazepine) | 522.3 |
| 140 | H | H | CH₂CH₃ | H | (benzazepine) | 501.4 |
| 141 | H | CH₃ | H | H | | 487.4 |
| 142 | H | H | Cl | H | | 507.3 |
| 143 | H | CH₃ | H | CH₃ | | 501.4 |
| 144 | H | H | H | H | | 475.3 |

-continued
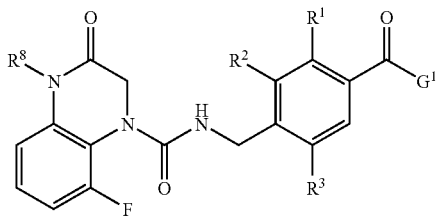
| Ex. | R[8] | R[1] | R[2] | R[3] | G[1] | MS (MH[+]) |
|---|---|---|---|---|---|---|
| 145 | H | H | CH$_2$CH$_3$ | H | 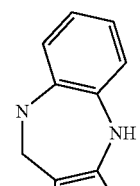 | 554.3 |
| 146 | H | H | Cl | H | 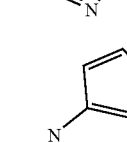 | 513.3 |
-continued
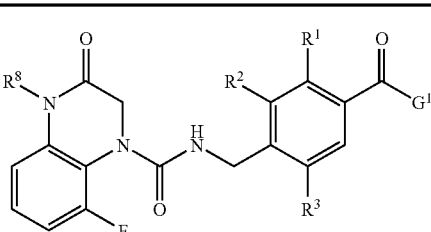
| Ex. | R[8] | R[1] | R[2] | R[3] | G[1] | MS (MH[+]) |
|---|---|---|---|---|---|---|
| 147 | CH$_3$ | H | H | H | 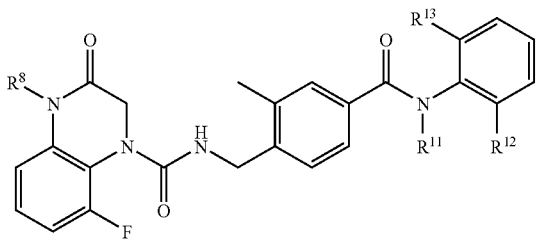 | 524.2 |
| Ex. | R[8] | R[11] | R[12] | R[13] | MS (MH[+]) |
|---|---|---|---|---|---|
| 148 | H | CH$_3$ | (3-methylpyrazol-1-yl) | H | 527.3 |
| 149 | H | CH$_3$ | (1-methyl-1,2,4-triazol-3-yl) | H | 528.6 |
| 150 | H | CH$_3$ | (1-methylimidazol-2-yl) | H | 527.7 |

-continued
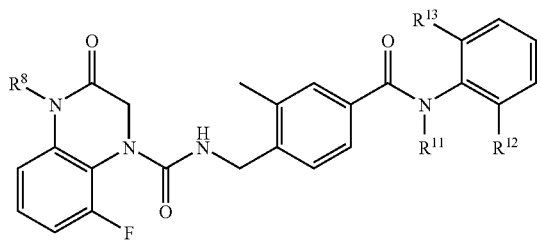
| Ex. | R[8] | R[11] | R[12] | R[13] | MS (MH+) |
|---|---|---|---|---|---|
| 151 | H | CH₃ | oxazol-2-yl | H | 514.4 |
| 152 | H | CH₃ | 1H-imidazol-2-yl | H | 513.1 |
| 153 | azetidin-1-yl-CH₂ | CH₃ | thiophen-2-yl | H | 612.3 |
| 154 | CH₃NH-CH₂ | CH₃ | thiophen-2-yl | H | 586.3 |
| 155 | pyrrolidin-1-yl-CH₂ | CH₃ | thiophen-2-yl | H | 626.4 |
| 156 | OHC-CH₂ | CH₃ | thiophen-2-yl | H | 571.1 |
| 157 | (CH₃)₂N-CH₂ | CH₃ | thiophen-2-yl | H | 600.1 |
| 158 | HOOC-CH₂ | CH₃ | thiophen-2-yl | H | 587.1 |
| 159 | H | CH₃ | pyridin-2-yl | H | 524.1 |

-continued
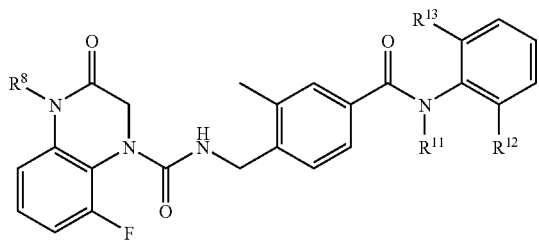
| Ex. | R⁸ | R¹¹ | R¹² | R¹³ | MS (MH⁺) |
|---|---|---|---|---|---|
| 160 | tert-butyl-O-C(O)-CH₂- | CH₃ | 2-thienyl | H | 643.1 |
| 161 | HO-CH₂- | CH₃ | 3-thienyl | H | 573.4 |
| 162 | H | CH₃ | 3-thienyl | H | 529.4 |
| 163 | HO-CH₂- | cyclopropyl | 2-thienyl | H | 599.3 |
| 164 | H | CH₃ | CH₂CH₂CH₃ | H | 475.3 |
| 165 | H | CH₃ | 2-thienyl | H | 515.6 |
| 166 | H | CH₃ | CH₂OH | H | 477.6 |
| 167 | HO-CH₂- | cyclopropyl | CH₂CH₂CH₃ | H | 559.7 |
| 168 | H | CH₃ | CHO | H | 475.4 |
| 169 | H | 2-thienyl | CH₃ | H | 529.3 |
| 170 | H | cyclopropyl | 2-thienyl | H | 555.3 |
| 171 | H | CH₃ | piperidin-1-yl | H | 530.4 |

-continued
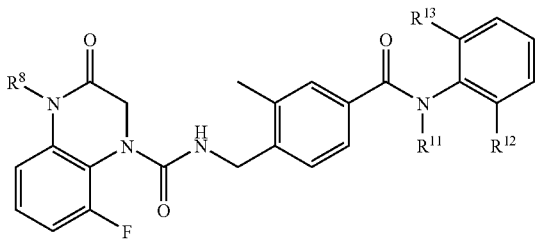
| Ex. | R⁸ | R¹¹ | R¹² | R¹³ | MS (MH⁺) |
|---|---|---|---|---|---|
| 172 | H | CH₃ | morpholinyl | H | 532.4 |
| 173 | H | CH₃ | benzimidazolyl | H | 563.4 |
| 174 | H | CH₃ | 1,2,4-triazolyl | H | 514.3 |
| 175 | H | CH₃ | imidazolyl | H | 513.3 |
| 176 | H | CH₃ | indolyl | H | 562.3 |
| 177 | H | CH₃ | pyrrolyl | H | 512.3 |
| 178 | H | CH(CH₃)₂ | thienyl | H | 557.3 |
| 179 | HO-CH₂ | CH₃ | thiazolyl | H | 574.3 |
| 180 | H | cyclopropyl | CH₃ | H | 487.3 |

-continued
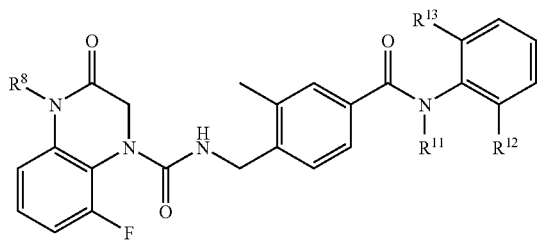
| Ex. | R⁸ | R¹¹ | R¹² | R¹³ | MS (MH⁺) |
|---|---|---|---|---|---|
| 181 | H | CH₃ | thiazol-2-yl | H | 530.2 |
| 182 | H | CH₃ | furan-2-yl | H | 513.3 |
| 183 | H | CH₂CH₂OH | CH₃ | H | 491.3 |
| 184 | H | CH₃ | CH₂CH₂CH₃ | H | 489.4 |
| 185 | H | CH₃ | Br | H | 525.5 |
| 186 | HOCH₂CH₂ | CH₃ | thiophen-2-yl | H | 573.2 |
| 187 | H | CH₃ | NH₂ | H | 462.3 |
| 188 | H | CH₃ | thiophen-2-yl | H | 529.4 |
| 189 | H | CH₃ | benzothiophen-2-yl | H | 579.3 |
| 190 | H | CH₃ | naphthalen-2-yl | H | 573.4 |
| 191 | H | CH₃ | phenyl | H | 523.4 |

-continued
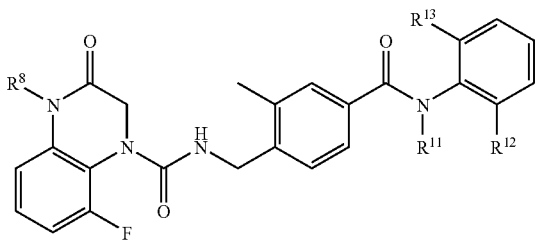
| Ex. | R8 | R11 | R12 | R13 | MS (MH+) |
|---|---|---|---|---|---|
| 192 | H | -CH2CH2-(2-thienyl) | CH3 | H | 557.3 |
| 193 | H | -CH2-(2-furyl) | CH3 | H | 527.4 |
| 194 | H | CH3 | CH2CH3 | H | 475.2 |
| 195 | H | -CH2-(2-thienyl) | CH3 | H | 543.3 |
| 196 | H | CH2CH3 | CH3 | H | 475.3 |
| 197 | H | CH2CH2CH3 | CH3 | H | 489.4 |
| 198 | CH3 | CH3 | CH3 | H | 475.5 |
| 199 | H | COOH | CH3 | H | 491.6 |
| 200 | H | COOCH3 | CH3 | H | 505.7 |
| 201 | HO-CH2- | CH3 | CH(CH3)2 | H | 533.7 |
| 202 | HO-CH2- | CH3 | CH3 | H | 505.6 |
| 203 | HO-C(O)-CH2- | CH3 | CH3 | H | 519.6 |
| 204 | tBuO-C(O)-CH2- | CH3 | CH3 | H | 575.5 |
| 205 | H | CH3 | CH3 | H | 461.6 |
| 206 | HO-CH2- | CH3 | N(CH3)2 | H | 534.6 |
| 207 | HO-C(O)-CH2- | CH3 | N(CH3)2 | H | 548.6 |
| 208 | tBuO-C(O)-CH2- | CH3 | N(CH3)2 | H | 604.6 |
| 209 | H | CH3 | N(CH3)2 | H | 489.9 |

-continued
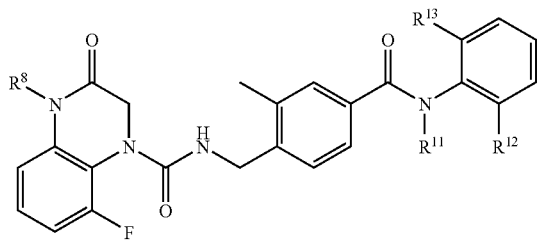
| Ex. | R[8] | R[11] | R[12] | R[13] | MS (MH+) |
|---|---|---|---|---|---|
| 210 | H | CH₃ | 2-thienyl | F | 547.4 |
| 211 | H | CH₃ | CHF₂ | H | 497.3 |
| 212 | H | CH₃ | CH(OCH₃)₂ | H | |
| 213 | H | CH₃ | 5-(pyridin-2-yl)thiophen-2-yl | H | 606.3 |
| 214 | H | CH₃ | 3-(trifluoromethyl)phenyl | H | 591.4 |
| 215 | H | CH₂CH₂OPh | CH₃ | H | 567.3 |
| 216 | H | CH₂CH₂CH₂NH₂ | CH₃ | H | 504.3 |
| 217 | H | CH₂C(O)OC(CH₃)₃ | CH₃ | H | 561.3 |
| 218 | H | CH₃ | C(O)NHCH₂-(2-thienyl) | H | 586.4 |

-continued

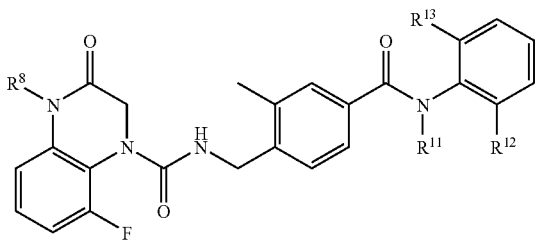

| Ex. | R⁸ | R¹¹ | R¹² | R¹³ | MS (MH⁺) |
|---|---|---|---|---|---|
| 219 | H | $CH_3$ | 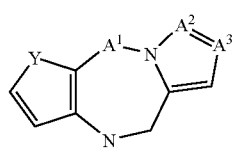 | H | 572.5 |

Example 220

Determination of $V_2$ Receptor Agonist Activity In Vitro

V2 receptor agonist activity was determined for all compounds and all the compounds of the invention cause significant cellular activation at concentrations of 30 μM or less. Preferred compounds cause significant activation at concentrations of 300 nM or less and can induce the same maximal effect as AVP.

Example 221

Pharmaceutical Composition for Tablet

Tablets containing 100 mg of the compound of Example 43 as the active agent are prepared from the following:

| | |
|---|---|
| Compound of Example 43 | 200.0 g |
| Corn starch | 71.0 g |
| Hydroxypropylcellulose | 18.0 g |
| Carboxymethylcellulose calcium | 13.0 g |
| Magnesium stearate | 3.0 g |
| Lactose | 195.0 g |
| Total | 500.0 g |

The materials are blended and then pressed to give 2000 tablets of 250 mg, each containing 100 mg of the compound of Example 43.

The foregoing Examples demonstrate that compounds within the scope of the invention are readily prepared using standard chemical techniques, and that these compounds have the biological properties that would be expected of $V_2$ receptor agonists. Thus it is clear that they may be useful in the treatment of human diseases that are currently treatable with desmopressin, such as central diabetes insipidus, nocturnal enuresis and nocturia. It has further been suggested that antidiuretics such as desmopressin may be useful in certain types of urinary incontinence. These arguments would also extend to the compounds of the present invention.

Desmopressin is also used in the treatment of certain coagulation disorders. There is good evidence to suggest that this action is also mediated through the $V_2$ receptor (see for example J E Kaufmann et al., "Vasopressin-induced von Willebrand factor secretion from endothelial cells involves $V_2$ receptors and cAMP", *J. Clin. Invest.* 106, 107-116, 2000; A Bernat et al., "$V_2$ receptor antagonism of DDAVP-induced release of hemostasis factors in conscious dogs", *J. Pharmacol. Exp. Ther.* 282, 597-602, 1997), and hence it would be expected that the compounds of the present invention should be useful procoagulants.

All the cited references are hereby incorporated by reference in their entirety.

The invention claimed is:

1. A compound according to formula 1, or a compound which is a tautomer or a pharmaceutically acceptable salt thereof,

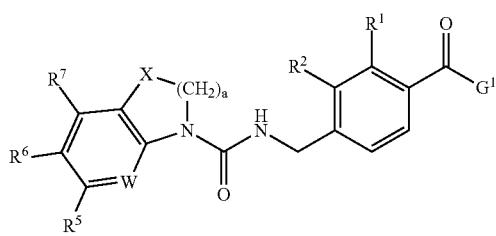

wherein:
W is selected from N and $CR^4$;
X is selected from $CH(R^8)$, O, S, $N(R^8)$, C(=O), C(=O)O, C(=O)$N(R^8)$, OC(=O), $N(R^8)$C(=O), $C(R^8)$=CH, and $C(=R^8)$;
$G^1$ is a bicyclic or tricyclic fused azepine derivative selected from general formulae 2 to 9 or an aniline derivative according to general formula 10

2

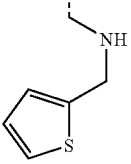

$R^1$ and $R^2$ are independently selected from H, F, Cl, Br, alkyl, $CF_3$, and O-alkyl;

$R^3$ is selected from H and alkyl;

$R^4$-$R^7$ are independently selected from H, F, Cl, Br, alkyl, $CF_3$, OH, and O-alkyl;

$R^8$ is selected from H, $(CH_2)_bR^9$, and $(C=O)(CH_2)_bR^9$;

$R^9$ is selected from H, alkyl, optionally substituted aryl, optionally substituted heteroaryl, OH, O-alkyl, OC(=O)alkyl, $NH_2$, NHalkyl, $N(alkyl)_2$, CHO, $CO_2H$, $CO_2$alkyl, $CONH_2$, CONHalkyl, $CON(alkyl)_2$, and CN;

$R^{10}$ is selected from H, alkyl, COalkyl, and $(CH_2)_dOH$;

$R^{11}$ is selected from alkyl, $(CH_2)_dAr$, $(CH_2)_dOH$, $(CH_2)_dNH_2$, $(CH_2)_dCOOalkyl$, $(CH_2)_dCOOH$, and $(CH_2)_dOAr$;

$R^{12}$ and $R^{13}$ are each independently selected from H, alkyl, F, Cl, Br, $CH(OCH_3)_2$, $CHF_2$, $CF_3$, COOalkyl, CONHalkyl, $(CH_2)_dNHCH_2Ar$, $CON(alkyl)_2$, CHO, COOH, $(CH_2)_dOH$, $(CH_2)_dNH_2$, $N(alkyl)_2$, $CONH(CH_2)_dAr$, and Ar;

Ar is selected from optionally substituted heterocycles or optionally substituted phenyl;

a is selected among 1, 2 and 3;

b is selected among 1, 2, 3 and 4;

c is selected among 0, 1 and 2; and d is selected among 0, 1, 2 and 3.

2. The compound according to claim 1, wherein $G^1$ is selected from

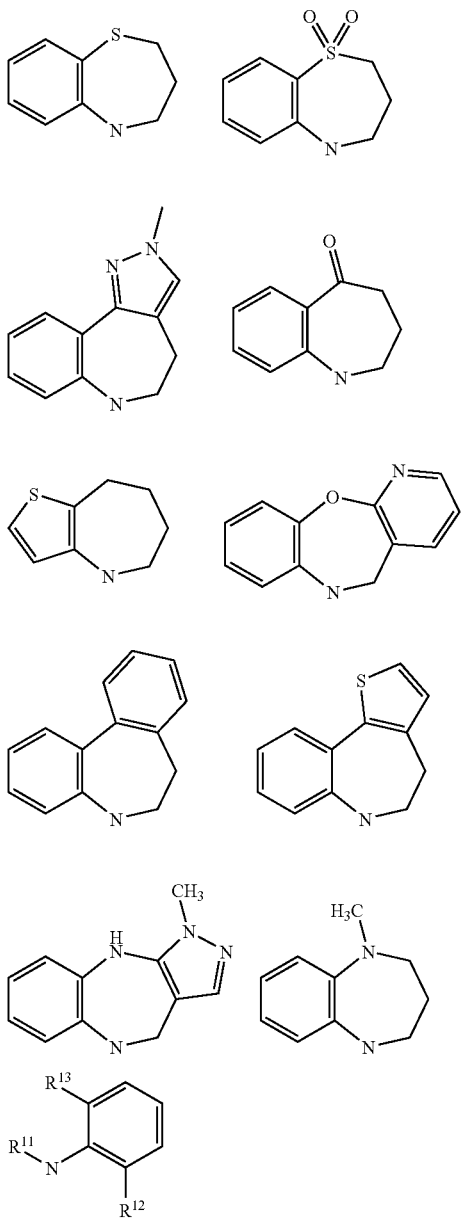

wherein R¹¹, R¹² and R¹³ are as previously defined.

3. The compound according to claim 2, wherein G¹ is selected from

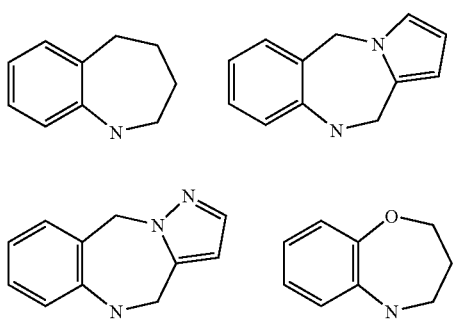

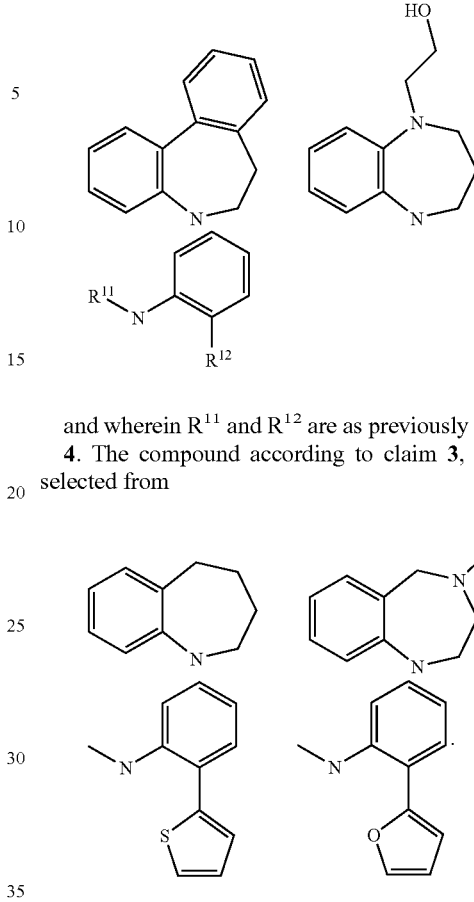

and wherein R¹¹ and R¹² are as previously defined.

4. The compound according to claim 3, wherein G¹ is selected from

5. The compound according to claim 1, wherein at least one of R¹, R², and R³ is not H.

6. The compound according to claim 5, wherein one of R¹, R², and R³ is methyl, Cl or F, and the rest are H.

7. The compound according to claim 6, wherein R² is methyl or Cl, and R¹ and R³ are both H.

8. The compound according to claim 1, wherein W is C—F, C—Cl or C—Br.

9. The compound according to claim 8, wherein W is C—F.

10. The compound according to claim 1, wherein X is N(R⁸)C(=O), and a is 1.

11. The compound according to claim 10, wherein X is N(R⁸)C(=O), R⁸ is (CH₂)ᵦR⁹, and a is 1.

12. The compound according to claim 1, wherein R.sup.5 is either H or F, and both R⁶ and R⁷⁷ are H.

13. The compound according to claim 1, wherein W is CR⁴, X is N(R⁸)C(=O), R¹ is H, R² is methyl or Cl, R³ is H, R⁴ is F, and R⁵, R⁶6, and R⁷ are H, and a is 1.

14. The compound according to claim 1, wherein G¹ is a group according to general formula 7 wherein Y is CH=CH, A¹⁶ is CH₂, A¹⁷ is CH₂, R¹ is H, R² is methyl or Cl, and R³ is H.

15. The compound according to claim 1, wherein G.¹ is a group according to general formula 2, and wherein Y is CH=CH, A¹ is CH₂, both A² and A³ are CH, R¹ is H, R² is methyl or Cl, and R³ is H.

16. The compound according to claim 1 selected from
{1-[4-(5H,11H-Benzo[e]pyrrolo[1,2-a][1,4]diazepine-10-carbonyl)-2-methylbenzylcarbamoyl]-8-fluoro-1,2,3,4-tetrahydroquinolin-4-yl}acetic acid ethyl ester;

{4-[4-(5H,11H-Benzo[e]pyrrolo[1,2-a][1,4]diazepine-10-carbonyl)-2-methylbenzylcarbamoyl]-5-fluoro-2-oxo-3,4-dihydro-2H-quinoxalin-1-yl}acetic acid methyl ester;
{5,6-Difluoro-4-[2-methyl-4-(2,3,4,5-tetrahydrobenzo[b]azepine-1-carbonyl)benzylcarbamoyl]-2-oxo-3,4-dihydro-2H-quinoxalin-1-yl}acetic acid;
{5-Chloro-4-[2-methyl-4-(2,3,4,5-tetrahydrobenzo[b]azepine-1-carbonyl)benzylcarbamoyl]-2-oxo-3,4-dihydro-2H-quinoxalin-1-yl}acetic acid;
{5-Fluoro-4-[2-methyl-4-(2,3,4,5-tetrahydrobenzo[b]azepine-1-carbonyl)benzylcarbamoyl]-2-oxo-3,4-dihydro-2H-quinoxalin-1-yl}acetic acid;
{6-Fluoro-5-[2-methyl-4-(2,3,4,5-tetrahydrobenzo[b]azepine-1-carbonyl)benzylcarbamoyl]-2-oxo-2,3,4,5-tetrahydrobenzo[b][1,4]diazepin-1-yl}acetic acid;
4-(3-Aminopropyl)-8-fluoro-3-oxo-3,4-dihydro-2H-quinoxaline-1-carboxylic acid 2-methyl-4-(2,3,4,5-tetrahydrobenzo[b]azepine-1-carbonyl)benzylamide;
4-Cyanomethyl-8-fluoro-3-oxo-3,4-dihydro-2H-quinoxaline-1-carboxylic acid 2-methyl-4-(2,3,4,5-tetrahydrobenzo[b]azepine-1-carbonyl)benzylamide;
4-Cyanomethyl-8-fluoro-3-oxo-3,4-dihydro-2H-quinoxaline-1-carboxylic acid 4-(5H,11H-benzo[e]pyrrolo[1,2-a][1,4]diazepine-10-carbonyl)-2-methylbenzylamide;
7,8-Difluoro-4-(2-hydroxyethyl)-3-oxo-3,4-dihydro-2H-quinoxaline-1-carboxylic acid 2-methyl-4-(2,3,4,5-tetrahydrobenzo[b]azepine-1-carbonyl)benzylamide;
7,8-Difluoro-4-(2-hydroxyethyl)-3-oxo-3,4-dihydro-2H-quinoxaline-1-carboxylic acid 4-(5H,11H-benzo[e]pyrrolo[1,2-a][1,4]diazepine-10-carbonyl)-2-methylbenzylamide;
8-Chloro-4-(2-hydroxyethyl)-3-oxo-3,4-dihydro-2H-quinoxaline-1-carboxylic acid 2-methyl-4-(2,3,4,5-tetrahydrobenzo[b]azepine-1-carbonyl)benzylamide;
8-Fluoro-3,4-dihydro-2H-quinoline-1-carboxylic acid 4-(5H,11H-benzo[e]pyrrolo[1,2-a][1,4]diazepine-10-carbonyl)-2-methylbenzylamide;
8-Fluoro-3-oxo-3,4-dihydro-2H-quinoxaline-1-carboxylic acid 2-chloro-4-(2,3,4,5-tetrahydrobenzo[b]azepine-1-carbonyl)benzylamide;
8-Fluoro-3-oxo-3,4-dihydro-2H-quinoxaline-1-carboxylic acid 4-(6,7-dihydrodibenzo[b,d]azepine-5-carbonyl)-2-methylbenzylamide;
8-Fluoro-3-oxo-3,4-dihydro-2H-quinoxaline-1-carboxylic acid 4-[5-(2-hydroxyethyl)-2,3,4,5-tetrahydrobenzo[b][1,4]diazepine-1-carbonyl]-2-methylbenzylamide;
8-Fluoro-3-oxo-4-(1H-tetrazol-5-ylmethyl)-3,4-dihydro-2H-quinoxaline-1-carboxylic acid 2-methyl-4-(2,3,4,5-tetrahydrobenzo[b]azepine-1-carbonyl)benzylamide;
8-Fluoro-3-oxo-4-(2-oxoethyl)-3,4-dihydro-2H-quinoxaline-1-carboxylic acid 2-methyl-4-(2,3,4,5-tetrahydrobenzo[b]azepine-1-carbonyl)benzylamide;
8-Fluoro-4-(2-hydroxyethyl)-3-oxo-3,4-dihydro-2H-quinoxaline-1-carboxylic acid 2-methyl-4-(2,3,4,5-tetrahydrobenzo[b]azepine-1-carbonyl)benzylamide;
8-Fluoro-4-(2-hydroxyethyl)-3-oxo-3,4-dihydro-2H-quinoxaline-1-carboxylic acid 4-(5H,11H-benzo[e]pyrrolo[1,2-a][1,4]diazepine-10-carbonyl)-2-methylbenzylamide;
8-Fluoro-4-(2-hydroxyethyl)-3-oxo-3,4-dihydro-2H-quinoxaline-1-carboxylic acid 4-(7,8-dihydro-6H-5-oxa-9-azabenzocycloheptene-9-carbonyl)-2-methylbenzylamide;
8-Fluoro-4-(2-methoxyethyl)-3-oxo-3,4-dihydro-2H-quinoxaline-1-carboxylic acid 4-(5H,11H-benzo[e]pyrrolo[1,2-a][1,4]diazepine-10-carbonyl)-2-methylbenzylamide;
8-Fluoro-4-(2-methylaminoethyl)-3-oxo-3,4-dihydro-2H-quinoxaline-1-carboxylic acid 2-methyl-4-(2,3,4,5-tetrahydrobenzo[b]azepine-1-carbonyl)benzylamide;
8-Fluoro-4-methyl-3-oxo-3,4-dihydro-2H-quinoxaline-1-carboxylic acid 2-methyl-4-(4H,10H-3,3a,9-triazabenzo[f]azulene-9-carbonyl)benzylamide;
8-Fluoro-4-methyl-3-oxo-3,4-dihydro-2H-quinoxaline-1-carboxylic acid 4-(5H,11H-benzo[e]pyrrolo[1,2-a][1,4]diazepine-10-carbonyl)-2-methylbenzylamide;
9-Fluoro-5-(2-hydroxyethyl)-4-oxo-2,3,4,5-tetrahydrobenzo[b][1,4]diazepine-1-carboxylic acid 2-methyl-4-(2,3,4,5-tetrahydrobenzo[b]azepine-1-carbonyl)benzylamide;
9-Fluoro-5-oxo-2,3-dihydro-5H-benzo[e][1,4]oxazepine-1-carboxylic acid 2-methyl-4-(2,3,4,5-tetrahydrobenzo[b]azepine-1-carbonyl)benzylamide;
9-Fluoro-5-oxo-2,3,4,5-tetrahydrobenzo[e][1,4]diazepine-1-carboxylic acid 2-methyl-4-(2,3,4,5-tetrahydrobenzo[b]azepine-1-carbonyl)benzylamide;
8-Fluoro-4-(2-hydroxyethyl)-3-oxo-3,4-dihydro-2H-quinoxaline-1-carboxylic acid 4-[(2-furan-2-ylphenyl)methylcarbamoyl]-2-methylbenzylamide; and
8-Fluoro-4-(2-hydroxyethyl)-3-oxo-3,4-dihydro-2H-quinoxaline-1-carboxylic acid 2-methyl-4-[methyl-(2-thiophen-2-ylphenyl)carbamoyl]benzylamide.

17. A pharmaceutical composition comprising a compound according to claim 1 as an active agent and at least one excipient.

18. A pharmaceutical composition according to claim 17, formulated for oral administration.

\* \* \* \* \*